(12) United States Patent
Jozefiak et al.

(10) Patent No.: US 11,090,354 B2
(45) Date of Patent: Aug. 17, 2021

(54) COMPOSITION AND METHOD FOR TREATMENT OF METABOLIC DISORDERS

(71) Applicant: The Johns Hopkins University, Baltimore, MD (US)

(72) Inventors: Thomas Jozefiak, Belmont, MA (US); Michael Parlato, Baltimore, MD (US); Pratik Patel, Worcester, MA (US); Kevin Colbert, Baltimore, MD (US); Ashish Nimgaonkar, Baltimore, MD (US); Pankaj Pasricha, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 57 days.

(21) Appl. No.: 15/750,460

(22) PCT Filed: Aug. 5, 2016

(86) PCT No.: PCT/US2016/045814
§ 371 (c)(1),
(2) Date: Feb. 5, 2018

(87) PCT Pub. No.: WO2017/024237
PCT Pub. Date: Feb. 9, 2017

(65) Prior Publication Data
US 2018/0228863 A1 Aug. 16, 2018

Related U.S. Application Data

(60) Provisional application No. 62/201,980, filed on Aug. 6, 2015.

(51) Int. Cl.
| | | |
|---|---|---|
| A61K 38/00 | (2006.01) | |
| A61K 38/02 | (2006.01) | |
| A61K 31/722 | (2006.01) | |
| A61K 31/79 | (2006.01) | |
| A61K 47/32 | (2006.01) | |
| A61K 9/00 | (2006.01) | |
| A61K 9/08 | (2006.01) | |
| A61K 47/36 | (2006.01) | |
| A61K 47/38 | (2006.01) | |
| A61K 47/34 | (2017.01) | |
| A61K 9/16 | (2006.01) | |
| A61K 9/20 | (2006.01) | |
| A61K 9/50 | (2006.01) | |
| A61K 47/26 | (2006.01) | |
| A61K 9/06 | (2006.01) | |
| A61K 9/48 | (2006.01) | |

(52) U.S. Cl.
CPC ............ *A61K 38/02* (2013.01); *A61K 9/0095* (2013.01); *A61K 9/06* (2013.01); *A61K 9/08* (2013.01); *A61K 9/16* (2013.01); *A61K 9/20* (2013.01); *A61K 9/50* (2013.01); *A61K 31/722* (2013.01); *A61K 31/79* (2013.01); *A61K 47/26* (2013.01); *A61K 47/32* (2013.01); *A61K 47/34* (2013.01); *A61K 47/36* (2013.01); *A61K 47/38* (2013.01); *A61K 9/48* (2013.01)

(58) Field of Classification Search
USPC ........................................................ 514/1.1
See application file for complete search history.

(56) References Cited

U.S. PATENT DOCUMENTS

| | | |
|---|---|---|
| 4,490,695 A | 12/1984 | de Ronde |
| 4,520,017 A | 5/1985 | Tunc |
| 4,623,539 A | 11/1986 | Tunc |
| 5,681,819 A | 10/1997 | Tang et al. |
| 5,900,247 A | 5/1999 | Rault et al. |
| 6,585,997 B2 | 7/2003 | Moro et al. |
| 7,976,870 B2 | 7/2011 | Berner et al. |
| 8,642,088 B2 | 2/2014 | Reed et al. |
| 9,730,637 B2 | 8/2017 | Simberg et al. |
| 9,808,418 B2 | 11/2017 | Pillay et al. |
| 10,588,857 B2 | 3/2020 | Schentag et al. |
| 2002/0132008 A1 | 9/2002 | Mumper et al. |
| 2003/0060486 A1 | 3/2003 | Jacob et al. |
| 2007/0014756 A1 | 1/2007 | Touchot |
| 2009/0011019 A1 | 1/2009 | Jabagirder et al. |
| 2011/0305768 A1 | 12/2011 | Mao et al. |
| 2012/0143348 A1 | 6/2012 | Voegele |
| 2012/0282343 A1 | 11/2012 | Leong et al. |
| 2013/0337022 A1 | 12/2013 | Pillay et al. |
| 2013/0344147 A1 | 12/2013 | Kalnose et al. |
| 2014/0288398 A1 | 9/2014 | Simberg et al. |
| 2016/0022729 A1 | 1/2016 | Karp et al. |

FOREIGN PATENT DOCUMENTS

| | | | |
|---|---|---|---|
| WO | WO 2000/05974 A1 | 2/2000 | |
| WO | WO 2014/151565 A1 | 9/2014 | |
| WO | WO-2014151565 A1 * | 9/2014 | ............ A61K 33/20 |

OTHER PUBLICATIONS

Extended European Search Report dated Mar. 7, 2019, regarding EP 16 833 940.6.

* cited by examiner

*Primary Examiner* — Jeanette M Lieb
(74) *Attorney, Agent, or Firm* — DLA Piper LLP (US)

(57) ABSTRACT

The present invention provides compositions and methods for treatment of metabolic syndromes. Namely, the presently disclosed compositions and methods are provided for affecting the function of the gastrointestinal endocrine system in key regions of the gut, thereby, producing therapeutic effects on obesity, diabetes and other metabolic disorders. The compositions include components for forming luminal barriers within the gastrointestinal tract of a subject where the barrier is created in-situ via interaction of resident mucin with the mucin-interacting agent.

13 Claims, 21 Drawing Sheets

Turbidity of choice polymers as a function of concentration.

Turbidity of Low Molecular Weight chitosan as a function of polymer and mucin concentration.

Turbidity of Medium Molecular Weight chitosan as a function of polymer and mucin concentration.

Impermeability measurements of low and medium molecular weight chitosan over a range of polymer concentrations.

Efficacy of 1% Chitosan (4 bolus, Duodenal Cannula).

Efficacy of 1% Chitosan (2 bolus, Duodenal Cannula).

Impermeability measurements of various high molecular weight chitosans with varying percentages of deacetylation.

Influence of pH and chitosan molecular weight on polymer-mucin turbidity.

COMPOSITION AND METHOD FOR TREATMENT OF METABOLIC DISORDERS

CROSS-REFERENCE TO RELATED APPLICATIONS

This application is a National Stage under 35 U.S.C. § 371 of PCT application PCT/US2016/045814 designating the United States and filed on Aug. 5, 2016, which claims the benefit of priority under 35 U.S.C. § 119(e) of U.S. Provisional Patent Application Ser. No. 62/201,980, filed Aug. 6, 2015, the entire contents of which are incorporated herein by reference in their entireties.

STATEMENT OF GOVERNMENT RIGHTS

This invention was made with government support under 1521347 awarded by the National Science Foundation. The government has certain rights in the invention.

BACKGROUND OF THE DISCLOSURE

Field of the Disclosure

The invention relates generally to therapeutic compositions and more specifically to luminal barrier forming compositions and methods for use thereof in the treatment of metabolic disorders.

Background Information

Twenty-two percent of the 27 million patients with Type II diabetes mellitus (T2DM) in the United States are unable to control the disease despite being on intensive medical therapies. These patients are unable to keep their hemoglobin A1c (HbA1c), an indicator of average blood glucose levels over a 3-month period, below the American Diabetes Association (ADA) recommended 7% threshold and are at greater risk for heart disease, stroke and kidney disease. Further, patients with diabetes sometimes hesitate to begin insulin therapy despite the clinical rationale for its necessity. One retrospective study of 80,000 cases showed that patients and providers hesitate 7 years on average before beginning insulin as a therapy.

Analysis of the typical diabetic patient's path from first line drugs to insulin and on to surgery and other last resort treatments reveals striking gaps, not limited to ineffective treatments and clinical inertia. Surgery and other solutions also have failed to achieve wide adoption. The addition of specialist clinicians in the care pathway has contributed to those failures. Accordingly, an effective treatment in the hands of the primary care physician would likely reach a much larger segment of the patient population than those which require a specialist, such as an endocrinologist, a gastroenterologist, or a surgeon.

SUMMARY OF THE DISCLOSURE

In one aspect, the presently disclosed subject matter provides a method for applying a physical barrier to the gastrointestinal (GI) tract of a subject between the intestinal lining and the luminal contents. The method includes administering to the GI tract of the subject a composition having a mucin-interacting agent. The physical barrier is created in-situ by interaction of resident mucin in the GI tract with the mucin-interacting agent.

In a further aspect, the disclosure provides a method for targeting a physical barrier forming composition to the duodenum of a subject. The method includes orally administering a composition of the disclosure to the subject.

In various embodiments, the physical barrier can provide full or partial coverage of a region, may have varying degrees of permeability, and may be present in varying amounts and regions of the GI tract, such as the duodenum or portions thereof, such as the proximal duodenum. The physical barrier is formed of a composition includes one or more mucin-interacting agents that may be delivered via a plurality of forms, such as in a syrup, a gel, a liquid, a powder, and any combination thereof. In more particular embodiments, the formed barrier disrupts one or more signaling pathways in the GI tract excluding contact with luminal contents. The one or more signaling pathways may be interrupted without significantly interfering with nutrient absorption.

In another aspect, the disclosure provides a composition for forming a physical barrier in the gastrointestinal (GI) tract of a subject between the intestinal lining and the luminal contents. The composition includes a mucin-interacting agent, wherein the physical barrier is created in-situ by interaction of resident mucin in the GI tract and the mucin-interacting agent. The compositions are useful for treating metabolic disorders, such as insulin resistance or T2DM in a human subject. In embodiments, the compositions are capable of forming an occlusive intestinal coating in the proximal small intestine. In various embodiments the mucin-interacting agent is one or more mucin-complexing agents, mucin-thickening agents, or derivatives and combinations thereof. In some embodiments, the compositions contain components which enable the composition to adhere to the mucin-coated luminal wall. Other compositions of the disclosure include mucin-complexing components capable of combining with the endogenous mucin present on the luminal wall to form an in-situ mucin-polymer complex that functions as a component of the occlusive coating. Other compositions contain mucin-thickening agents which diminish the permeability of the intestinal mucin layer. Certain compositions contain combinations mucin-complexing and mucin-thickening components.

As discussed herein, the occlusive, in-situ, barrier-forming compositions are administered in various dosage forms. In one embodiment the composition is delivered as a therapeutic capsule or a tablet administered orally to a patient. In some embodiments, the capsule contains the active composition in the form of a rapidly dissolving solid powder. In some embodiments, the capsule dissolves quickly in the stomach enabling the solid powder composition to hydrate or dissolve quickly and be exposed to the proximal duodenum as a viscous fluid. In another embodiment the capsule contains the active composition as a viscous fluid. In some embodiments, the capsule provides enteric properties protecting the solid or liquid composition from gastric acidity and targeting delivery of the composition to the proximal small intestine. In another embodiment, the composition is provided as a fluid or syrup for direct oral administration to the human subject. In another embodiment the composition is provided in a sachet and is mixed with water or a beverage for a human subject to drink. In all cases, the composition is capable of forming an occlusive barrier, i.e., a physical barrier, in the proximal GI tract after administration of the dosage form to the human subject. In all cases, the therapeutic compositions are non-absorbed in the GI-tract, and are safely eliminated through excretion from the GI tract.

In yet another aspect, the disclosure provides a method for treating a metabolic disorder, such as, insulin resistance or T2DM, in a subject. The method includes administering a composition of the disclosure to the subject. The method achieves efficacy through the formation of an occlusive coating over the luminal surface of the proximal small intestine. The coating functions as a physical barrier and is sufficiently occlusive to minimize contact between the luminal wall and nutrient material passing through the lumen, thereby effectively treating the metabolic disorder. The occlusive coatings described in this invention are formed in-situ. The coatings are comprised of biocompatible, and nontoxic polymeric materials. The in-situ formed occlusive coatings of this disclosure function as a physical barrier in the upper GI tract, specifically the duodenum and optionally the stomach. The coating is not perfectly continuous, and occludes only a portion of the proximal GI tract, thereby not significantly interfering with or diminishing normal nutrient absorption. The coating is temporary, providing occlusion of the proximal duodenum for a period of time sufficient for efficacy, and is excreted through the GI tract without being absorbed.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

FIG. 20A is a fluorescent image of the chitosan intestinal lining (bright white) after treatment with a chitosan composition of the invention (image is taken 90 minutes post dosing in the rodent duodenum). FIG. 20B is a fluorescent image of intestinal lining as control.

DETAILED DESCRIPTION

Figure 1:
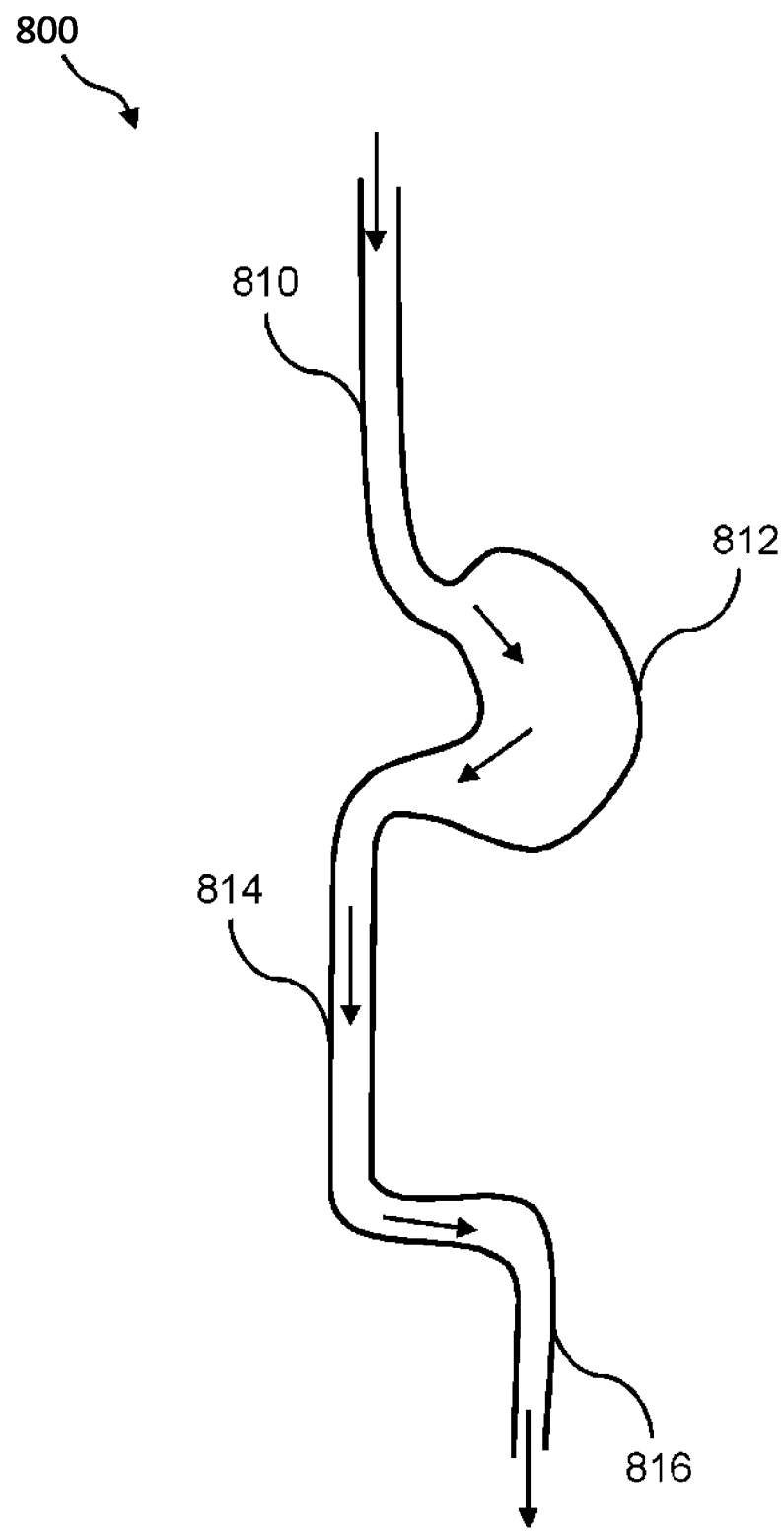
FIG. 1 illustrates a normal flow of luminal contents through a portion of gastrointestinal tract 800, e.g., a portion of the small intestine, through the stomach 812, duodenum 814, and jejunum 816.
Figure 2:
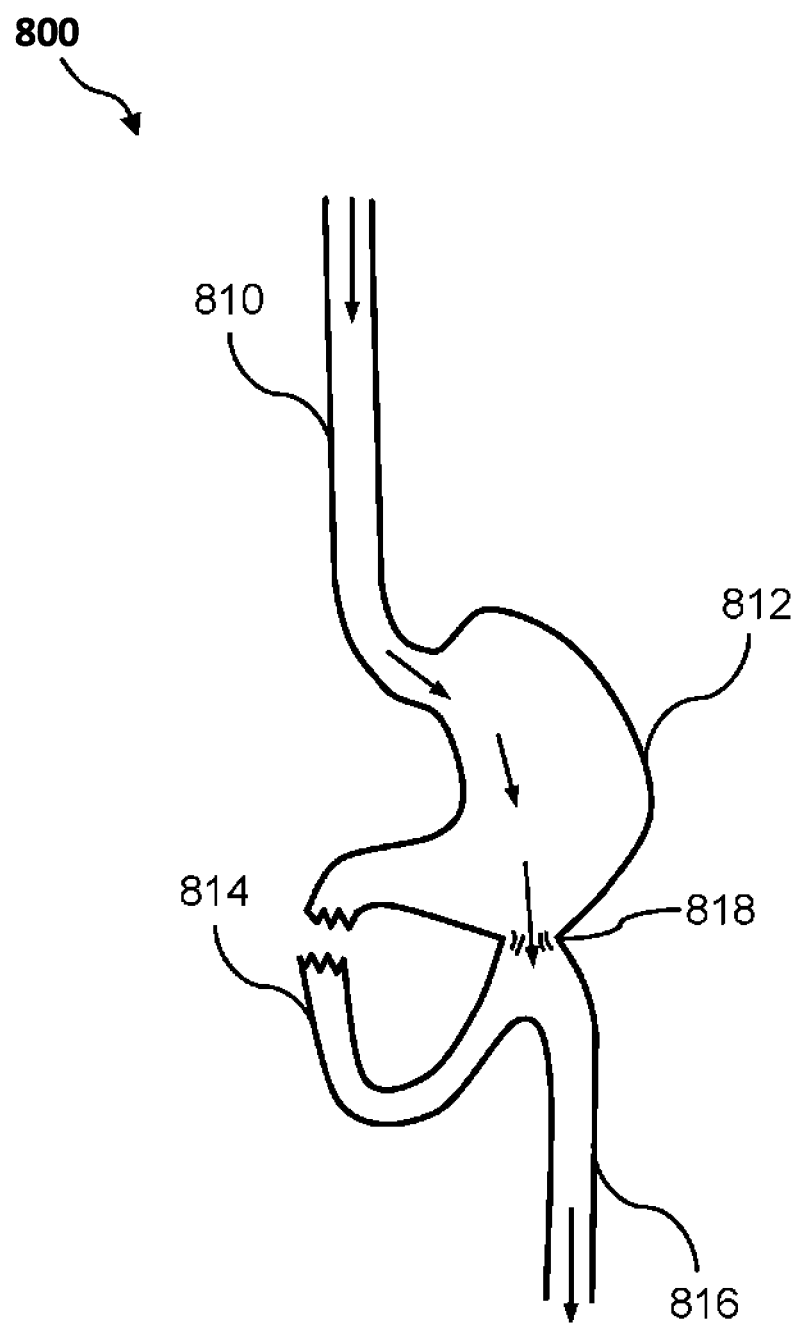
FIG. 2 illustrates flow of luminal contents following RYGB surgery where the luminal contents, e.g., food particles, no longer pass through the duodenum 814, but instead pass through Roux limb 818, wherein the surgery interrupts or alters certain neurohormonal signaling pathways in the proximal intestine, leading to diabetic remission.
Figure 3:
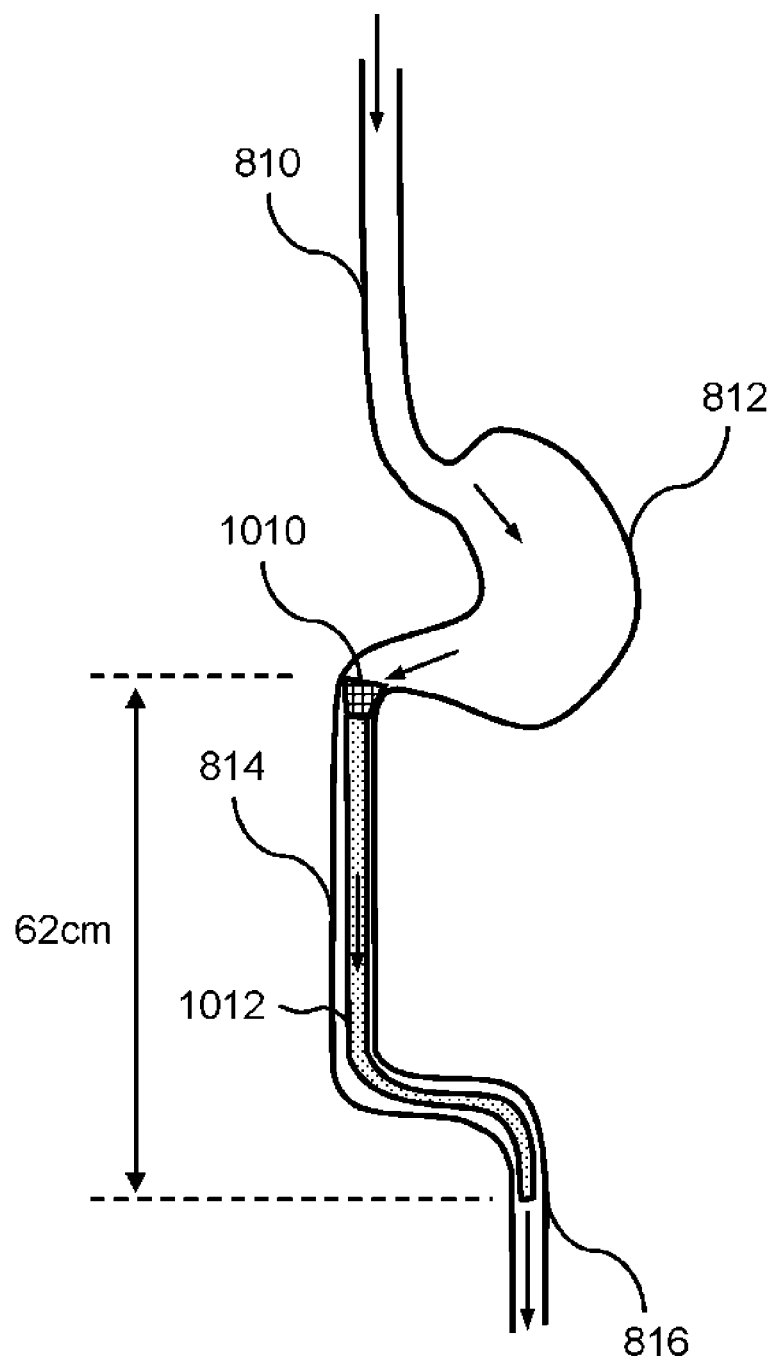
FIG. 3 illustrates preservation of nutrient absorption via a duodenal-jejunal bypass sleeve (DJBS) 1012 held in place by anchor 1010, e.g., a metal anchor, wherein, in this illustration nutrient absorption is blocked in duodenum 814 and jejunum 816 for 62 cm.
Figure 4:
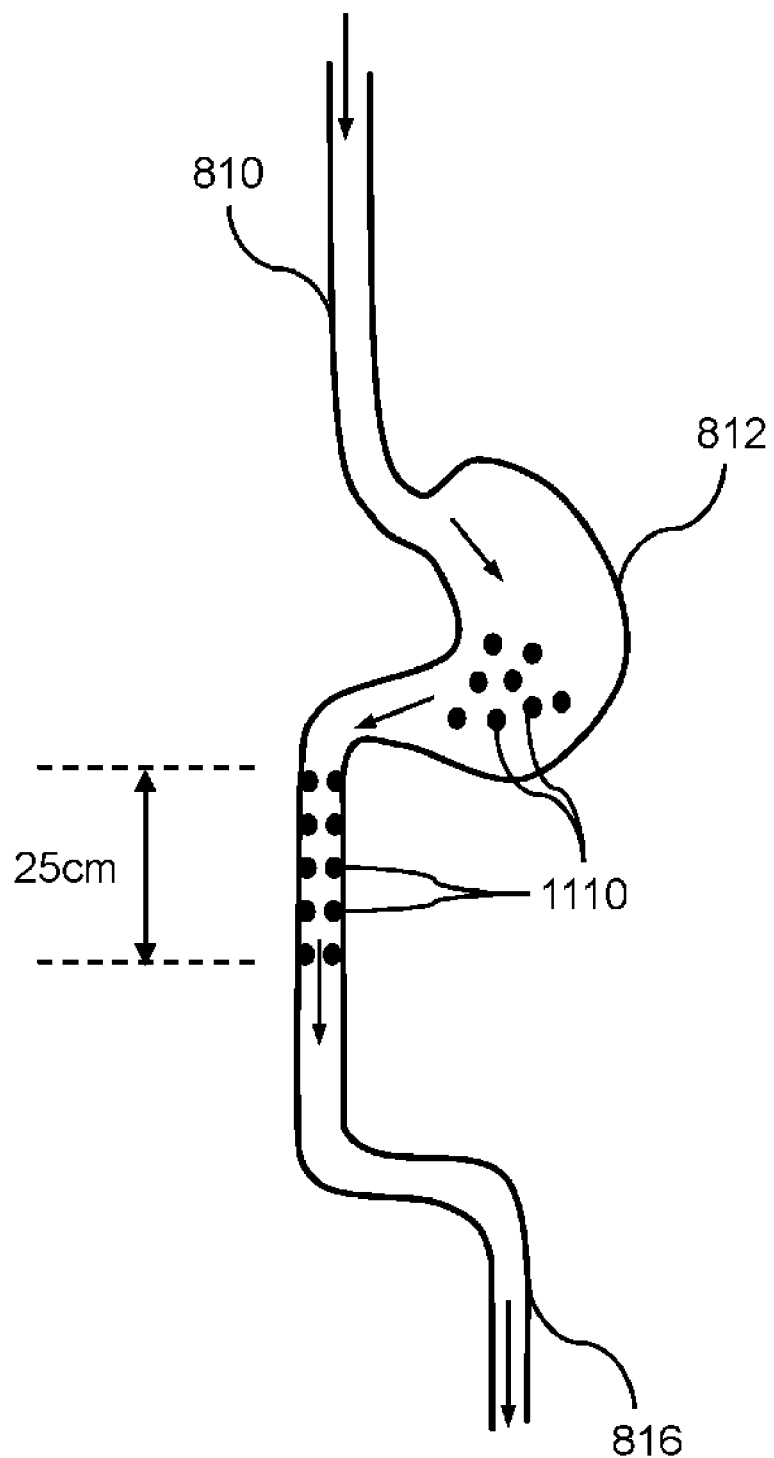
FIG. 4 illustrate preservation of nutrient absorption using the presently disclosed compositions 1110, in which in this representative example, a particular dosage can limit coverage to, for example, a 25-cm portion of the proximal intestines, thereby preserving nutrient absorption capacity. Key neurohormonal signaling pathways also are interrupted in this embodiment.
Figure 5:
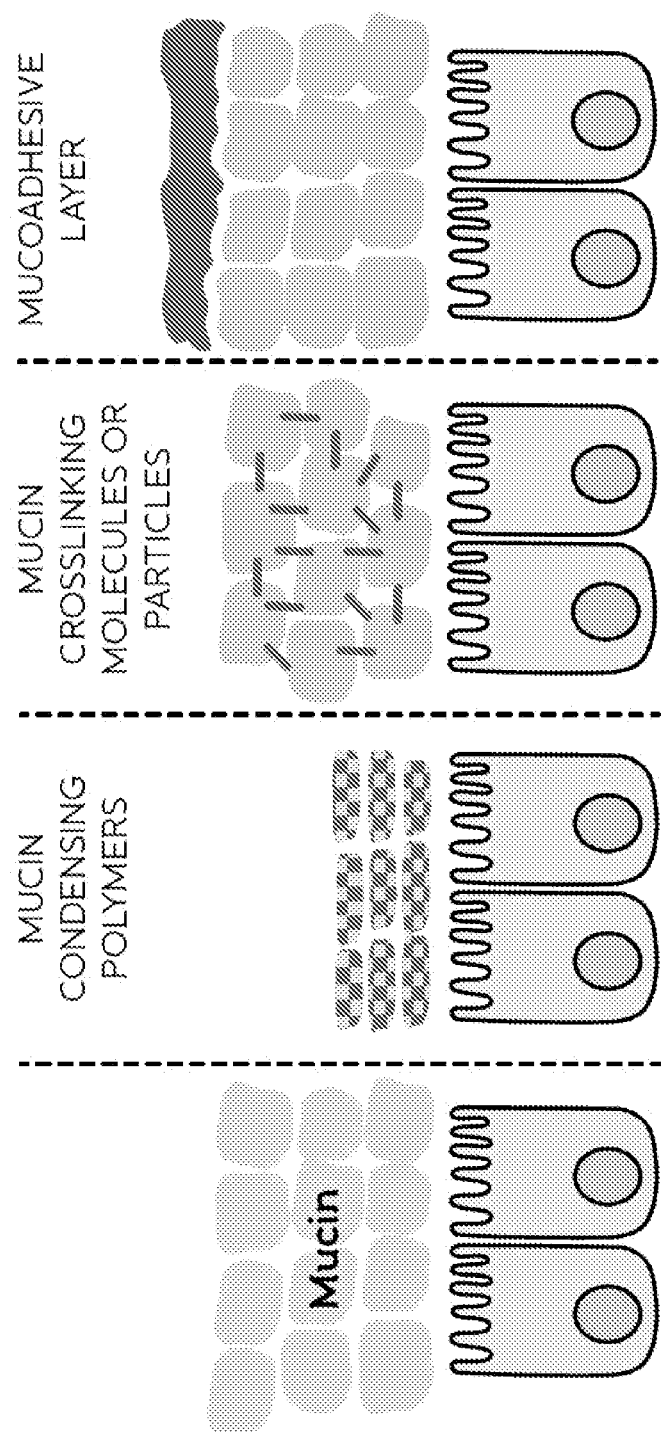
FIG. 5 is a schematic diagram illustrating mechanisms of action of mucin-interacting agents in barrier formation in various embodiments of the invention.

The presently disclosed subject matter now will be described more fully hereinafter with reference to the accompanying Drawings, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

T2DM has traditionally been treated with insulin therapy and oral hypoglycemics, which compound over a patient's lifetime, cause weight gain, and lead to greater insulin resistance. More recently, approaches for treating T2DM derived from bariatric surgery have been pursued as alternatives to traditional diabetic treatments. While the scientific community continues to investigate the exact mechanism of action by which these approaches work, it is indisputable that duodenal bypass results in glucose homeostasis. As evidenced by randomized clinical trials, roux-en-y gastric bypass (RYGB) leads to the complete remission of T2DM in >80% of patients.

While gastric bypass surgery is very effective, few patients meet the body mass index (BMI) requirements (greater than 35 kg/m$^2$) and are willing to risk the complications of the major (and costly) operation. Fewer than 200,000 bariatric surgeries are performed each year for obese patients with T2DM. Therefore, the remissive effects of the procedure are unavailable to 99% of diabetic patients. Other attempts have been made to provide alternative, less-invasive solutions with the introduction of the endoluminal sleeve and the mucosal resurfacing procedure, among others.

An example of the use of a bariatric sleeve to treat T2DM is a 62-cm flexible duodenal-jejunal bypass sleeve (DJBS) implanted in the intestines of a subject in need of treatment thereof for six to twelve months. The DJBS has been implanted in several thousands of patients in Europe, Chile, and Australia. The device results in remission of T2DM in more than 60% of patients. The implant, however, can cause adverse effects including nausea, vomiting, and discomfort. The DJBS implantation also requires patients to take nutrient supplements following the procedure.

The presently disclosed approach acts on a mechanism distinct from those approaches known in the art. Indeed, embodiments disclosed herein are designed to retain as much of the nutrient absorbing capacity of the duodenum as possible, while still resulting in a clinically significant effect on T2DM. This design consideration is made with the assumption that preserving the patient's ability to extract nutrients from sustenance is a desirable element of a treatment, and is based on the hypothesis that the primary mechanism in the efficacy of bariatric surgery is inhibition of neurohormonal signaling pathways as opposed to inhibited nutrient absorption.

As referred to herein, the phrase "preserving significant nutrient absorption" and variations thereof, is intended to mean retaining capacity for absorption such that the subject does not require nutritional supplements as a direct result of the treatment. Significant nutrient absorption may mean a level of nutrient absorption which is significantly higher when compared with those levels of nutrient absorption which occur in subjects as a result of procedures like the implantation of duodenal-jejunal bypass sleeve, for instance. Significant nutrient absorption should further be understood to include the absorption of nutrients such as carbohydrates, fats, proteins, vitamins or minerals. As disclosed herein below, "significant nutrient absorption" should further be understood to include such levels of nutrient absorption as might be demonstrable with a d-xylose blood absorption test in a normal subject.

Accordingly, the presently disclosed subject matter provides compositions for and methods of treatment of metabolic disorders. As used herein, the term "metabolic disorder" includes glucose intolerance, pre-diabetes, type 1 and type 2 diabetes, obesity, dyslipidemia, hypertension and insulin resistance. Namely, the presently disclosed compositions and methods are provided for affecting the function of the gastrointestinal endocrine system in particular regions of the duodenum, thereby, producing therapeutic effects on obesity, diabetes and other metabolic syndromes.

As used herein, the term "therapeutic effect" includes an effect or outcome that is desirable from the perspective of a physician, an effect which may be the goal of a procedure, such as, the implantation of the duodenal-jejunal bypass sleeve, a desirable effect that may be measured by a change in results on tests including, but not limited to, the fasting blood glucose, the oral glucose tolerance, hemoglobin A1c, and the like. The term "therapeutic effect" could further be construed to mean a desirable change in clinical parameters of a subject with a metabolic disorder.

Accordingly, in some aspects, the presently disclosed subject matter provides a method for applying a physical barrier to the gastrointestinal (GI) tract of a subject between the intestinal lining and the luminal contents. The method includes administering to the GI tract of the subject a composition having a mucin-interacting agent. The physical barrier is created in-situ by interaction of resident mucin in the GI tract with the mucin-interacting agent.

As used herein, the term "intestinal lumen" refers to the cavity of the intestines. Further, as used herein, the terms luminal contents or, more particularly, intraluminal contents should be understood to include chyme, alimentary flow, nutrients, and food particles inside the intestinal lumen. As used herein, the term "proximal small intestines" should be understood to mean the portion of the intestines generally defined as the duodenum. Proximal small intestine should further be understood to include the first 0 to 50 cm of the small intestines following the stomach. That is, ranges such as the first 10 cm, the first 20 cm, the first 30 cm, and the first 40 cm of the human intestine should be included by proximal small intestines. In particular embodiments, the physical barrier comprise a physical barrier which may exhibit varying levels of permeability, and which may be selectively permeable.

As used herein, the term "physical barrier" includes a structure that prevents the contact of one material with one or more other materials. For instance, a physical barrier may prevent the contact of the intraluminal contents (contents within the GI tract) with that of the lining and/or components within the wall of the GI tract. As used herein, the term "intestinal lining" refers to the lining of the wall of the GI tract which may comprise the mucosa and the mucus. Further, the term "partial" should be construed to mean having a degree of permeability greater than about 1, 5, 10, 25, 30, 40, 50% or more.

The physical barrier may be incomplete in preventing contact between one or more materials. Therefore, the physical barrier may further be partial, discontinuous, discrete and spatially distributed, may have varying degrees of permeability, and may be present in varying amounts and regions of the intestines. For instance, physical barrier may mean a semi-permeable liquid coating in contact with the mucus or mucins of the intestines.

In yet more particular embodiments, the method further comprises applying the physical barrier to limit an area of effective coverage on the lining of the GI tract to a section of the GI tract less than about 30 cm in length, wherein the section of the intestines begin at the pyloric sphincter and extends distally toward the jejunum. In particular embodiments, the physical barrier is applied to the GI tract starting in the duodenum with progressively increasing lengths from about 1 cm to about 30 cm, including 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30 cm, including any integer and fraction thereof, to have a dose dependent effect.

In some embodiments, the physical barrier is created when a mucin-interacting agent, such as a cationic compound combines in-situ with the anionic mucins lining the wall of the intestines. As used herein, the term "creating in-situ" and variations thereof, implies enabling the formation of the final embodiment locally of the intended barrier from constituent elements at the desired site, rather than in a pre-assembled manner.

As disclosed herein, the therapeutic compositions of the invention are comprised of materials capable of forming an occlusive, non-absorbed luminal barrier when administered to a subject. Key components of the compositions are mucin-interacting agents, such as mucin-complexing compounds and mucin-thickening compounds, compounds to enhance occlusion and minimize permeability of the barrier layer, and other components needed to enhance efficacy and ease of use for the therapeutic composition such as lubricants, viscosity modifying agents, coloring agents, taste and fragrance controlling agents. Some compounds in the compositions described herein may provide multiple functions, for example, certain compounds may function as mucoadhesive and mucin-complexing components.

In particular embodiments, the barrier forming component adheres to the mucosa of the GI tract for a retention period or residence time. As used herein, the terms "retention period" or "residence time" include time periods from ranging from half an hour to 7 days, including time period ranging from 1 hour to 3 hours, 1 hour to 5 hours, 1 hour to 24 hours, 1 to 3 days, and others.

The residence time of embodiments described in the disclosure can vary depending on the clinical application. For instance, up to 50% of patients with T2DM have gastroparesis, or delayed gastric emptying, that may require the mucoadhesive lining to remain in place for a longer time than a pre-diabetic or non-diabetic obese patient. Blood glucose levels spikes often within the first two hours of eating a meal, most often within the first 60 minutes; thus, the lining should adhere for a minimum for 60 minutes in one embodiment. In another embodiment, in the case of pre-diabetic patients who may not take medication prior to every meal, and thus may not comply with a treatment that would require to change their behavior, a longer lasting mucoadhesive lining may be required. In this application, the lining may adhere for a minimum of 6-8 hours with a maximum of 24 hours could be required. Residence time will also be influenced by the mucus layer at which the polymer develops the most affinity to. For instance, the superficial, loosely adherent layer sloughs off on the order of minutes to hours, whereas affinity to the deeper firmly adherent layer would lead to a longer lasting mucoadhesive coating. Overall, residence time can be tuned to various clinical and technical considerations in the embodiments outlined in this disclosure.

Mucin-complexing agents of the disclosure include polymeric compounds capable of complexing or condensing intestinal mucin to form a polyplex. In preferred cases, the resulting polyplex material will function as a component of the occlusive coating adherent on the intestinal wall. Exemplary mucin-complexing compounds of the therapeutic compositions include: chitosan, trimethyl chitosan, chitosan glycol, chitosan glycol trimethyl ammonium iodide, poly(lysine), ($\epsilon$-poly-L-lysine or EPL), poly(arginine), poly(histidine), poly(ornithine), chemically modified chitosan derivatives such as thiolated chitosan, high isoelectric point proteins such as basic whey protein or lysozyme, polyethyleneimine, hydroxyethylated polyethyleneimine, polyamidoamine (PAMAM) dendrimers, other cationic dendrimers, poly(allylamine) and its copolymers, crosslinked or chemically modified poly(allylamine) derivatives such as sevelamer and colesevelam, poly(diallylamine) and its copolymers, poly(diallyldimethylammonium chloride) and its copolymers, poly(vinylamine) and its copolymers, poly(vinylimidazole) and its copolymers, poly(vinylpyridine) and its copolymers, poly(vinylaniline) and its copolymers, amine containing acrylamide and methacrylamide copolymers, acrylamidopropyltrimonium chloride copolymers, poly[2-(dimethylamino)ethyl methacrylate copolymers, cationic gelatin derivatives, cationic dextran derivatives, cationic cellulose derivatives, cationic cyclodextrin derivatives, guar hydroxypropyltrimonium chloride, polyquaternium compounds used in the cosmetic and pharmaceutical industry. Cationic lipids used in the cosmetic and food industry such as lauric arginate. Preferred mucin-condensing components of the invention are: chitosan, hydroxyethylated poly(ethyleneimine), polylysine, cationic cellulose derivatives.

Mucin-thickening agents of the invention include compounds capable of establishing strong interactions or associations with mucin and provide a crosslinking function that stiffens the mucin and makes it less permeable. Exemplary mucin-thickening compounds of the compositions include: strong hydrogen bonding compounds epigallocatechin, tannic acid and tannin derivatives, gallic acid derivatives such as polymers or oligomers bearing two or more galloyl groups, catechol derivatives such as DOPA or dopamine and polymers or oligomers functionalized with two or more catechol groups, lectins, agglutinins, hemagglutinins such as wheat germ agglutinin, soybean agglutinin, jacalin lectin; micro- and nanoparticles including silica and modified silicas, silicate clays such as laponite, bentonite, hectorite, saponite, montmorillonites, and mixtures thereof, zinc oxide, titanium oxide, sucralfate; bismuth III carboxylate compounds including bismuth subsalycilate, bismuth subcitrate, bismuth gallate, bismuth neodecanoate; and liquid crystalline mixtures of diacylglycerols, triacylglycerols and phospholipids, for example glyceroldioleate/phosphatidylcholine. Preferred mucin-thickening components include laponite XLG, epigallocatechin, tannic acid and bismuth subsalycilate.

In various embodiments, a mucin-interacting agent may be formulated in a compositions at a concentration of greater than or equal to about 0.1, 0.5, 1, 2, 3, 4, 5, 6, 7, 8, 9 or 10% by weight.

Other components of the composition of this invention may include compounds, such as mucoadhesive agents, to enhance occlusion and minimize permeability of the in-situ formed coating layer, and other components such as lubricants, viscosity modifying agents, coloring agents, stabilizers, taste and fragrance controlling agents that may be needed to enhance efficacy and ease of use for the therapeutic composition.

Embodiments of this invention form an occlusive barrier layer in the proximal intestine, specifically the duodenum. In particularly preferred embodiments, the occlusive barrier is formed in the proximal duodenum or duodenal bulb. The compositions are therefore fully capable of forming a barrier layer immediately upon release from the stomach and presentation to the proximal duodenum. In some embodiments, the compositions are dosed in a liquid form and are sufficiently stable and soluble in the stomach allowing immediate delivery to the duodenum in an active state without requiring further swelling, solubilization, or equilibration with the surrounding milieu. Such compositions may also form a barrier layer while in the stomach. In other preferred embodiments, the active composition is dosed in a solid form capable of hydrating in the stomach. Slow dissolution provides some protection from gastric acidity, but these preferred materials remain capable of being presented to the early duodenum in a fully active state. In still other preferred embodiments, the active agents are dosed in a capsule or other enteric-coated dosage form capable of providing temporary protection from gastric acidity. In the case of a capsule or enteric-coated solid, the dosing form is engineered to allow release of the composition as soon as possible after or during passage through the pyloric valve. For example, enteric capsules have been described in the literature that are capable of targeting delivery to the duodenum.

While the stomach is known to present a highly acidic, low pH environment particularly in the fasted state, transit into the duodenum is accompanied by an increase in pH due to the presence of alkaline pancreatic juices. In preferred compositions, active agents of this invention are capable of responding to this increase in pH in a way that enhances interaction with mucin. For example, in some preferred embodiments the active agent becomes less well hydrated, less swollen, or less soluble as it experiences the pH increase in the duodenum. The loss of solubility/hydration at higher duodenal pH effectively allows the active agent to form a more occlusive layer, or a more occlusive (less soluble) mucin-complex under conditions presented in the duodenum. Without limiting the invention to a particular mechanism, preferred active agents of the invention are any mucin-complexing, mucin-binding, or mucoadhesive agent capable of efficiently forming occlusive barrier layers under conditions found in the proximal duodenum. Particularly preferred agents have activity targeted to the duodenum by demonstrating mucin-interacting properties that are enhanced by the pH increase from the stomach (pH=1.7, fasted) to the early duodenum (pH=6.1, fasted).

Preferred mucin-interacting agents of this invention that are targeted to the duodenum include polymeric amines such as polyethylenimine, poly(allylamine), and the like. These polymers remain highly charged even at duodenal pH, however, due to a high density of protonated amine sites in close proximity, they deprotonate to a small extent at duodenal pH. Even a small amount of neutralization effectively lowers the polymer charge density and causes these polymer chains become more coiled, compact, and less well hydrated as pH is increased. Other preferred polymers of this invention which are capable of responding to the pH increase of the duodenum are protonated polyamines that have inductive or structural features resulting in a lower pKa value than that of a standard protonated aliphatic amine. The lower pKa of these protonated polymers results in a greater sensitivity to the pH increase coincident with transit from the stomach to the duodenum. Polymers of this class are therefore targeted to interact with the lose mucin of the proximal duodenum. These include polyamines substituted with polar groups less than three carbon atoms away from the protonated amine. For example, chitosan and substituted derivatives, hydroxyethylated polyamines such as hydroxyethyl polyethylenimine, or glycidol-substituted polyamines. The general structural repeat unit for a beta-hydroxyl amine polymer is set forth as follows:

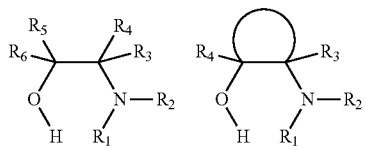

wherein R1-R6 can be independently H, Me, substituted or unsubstituted araalkyl groups.

The lower pKa of amines having a beta-hydroxyl group reflects intramolecular hydrogen bonding of the hydroxyl group to the amine nitrogen, decreasing electron density on the nitrogen. Shown below are several examples of duodenal-targeted polymeric amines preferred as mucin-interacting agents of this invention. Preferred protonated cationic polymers of this invention have pKa values less than 9.0. Particularly preferred cationic polymers of this invention have pKa values less than 7.0. The most preferred cationic polymers of this invention have pKa values less than or equal to 6.0. Another group of duodenal-targeted, pH-sensitive, mucin-interacting agents of this invention includes amine-functional polymers with an less basic nitrogen due to electronic delocalization of electron density on the nitrogen. For example, poly(vinylpyridine), poly(vinylimidazole), poly(vinyl aniline), and their derivatives or copolymers. Shown below are structural repeat units for several preferred mucin-interacting polymers with electronically delocalized amine nitrogen atoms.

Mucin-interacting beta-hydroxyl amine polymers include those having one or more structures as follows:

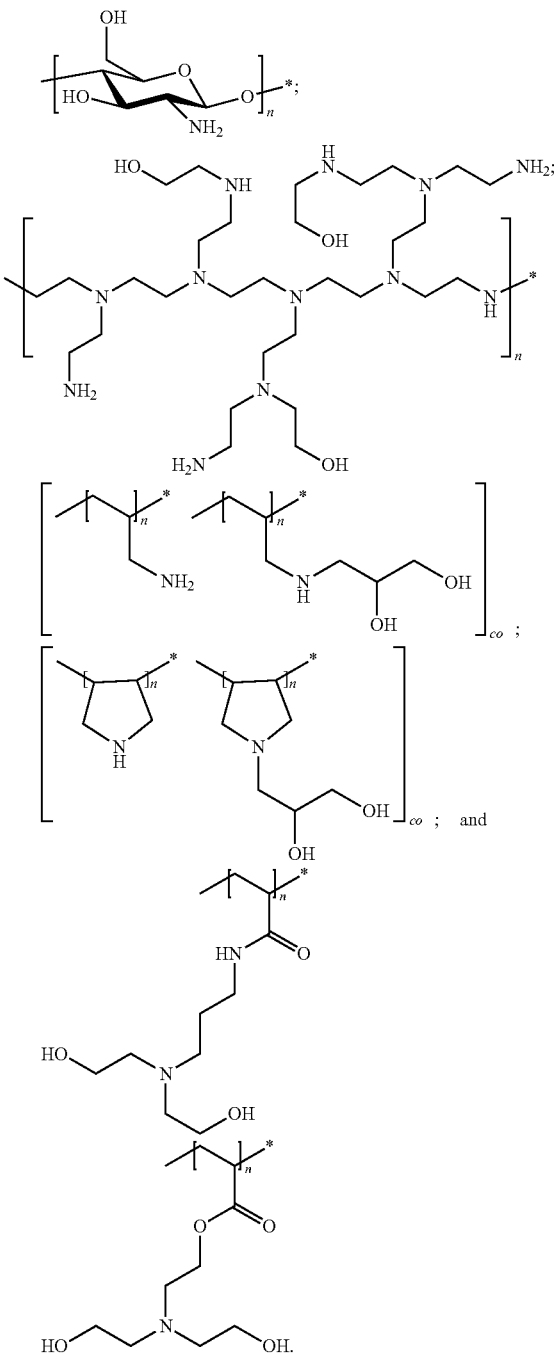

In some embodiments, mucin-interacting delocalized amine polymers include those having one or more structures as follows:

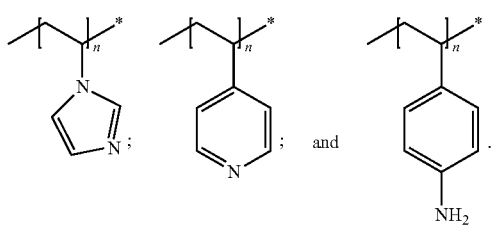

It is appreciated by those in the art that chitosan materials are a diverse set of polysaccharides varying in molecular weight from oligomers in the range of only 1,500 Da to high polymers with molecular weights of 1,000,000 Da and above. In addition, the deacetylation of chitin to form chitosan results in water soluble chitosan materials with variable degrees of deacetylation varying from 60% up to nearly 100%. Both molecular weight and degree of deacetylation have profound effects on the polymer's physical properties such as dissolution rate, solution viscosity, and cation density. These physical properties have a strong impact on the ability of the chitosan polymer to dissolve in the stomach, pass into the duodenum, and interact effectively with mucin in the upper GI tract. Unexpectedly the inventors have found that chitosans with high molecular weight are preferred embodiments of this invention. Chitosans with molecular weight greater than 25,000 and less than 1,000,000 are preferred. Chitosans with molecular weight greater than 90,000 Da and less than 600,000 Da are especially preferred, chitosans with molecular weight greater than 150,000 Da and less than 600,000 Da are most especially preferred. In embodiments, chitosan has a molecular weight greater than about 25, 50, 90, 130, 150, 190, 220, 310, 350, 400, 450, 500 or 550 kDa.

In addition, chitosans with a high degree of deacetylation are preferred embodiments of this invention. Chitosans with a degree of deacetylation >75% are preferred. Chitosans with a degree of deacetylation >85% are especially preferred. Chitosans with a degree of deacetylation >90% are most especially preferred. In embodiments, chitosans are utilized with a high degree of deacetylation greater than about 60, 65, 70, 75, 80, 85, 90 or 95%.

Some mucin-interacting materials for use in the present invention have been shown to form insoluble mucin complexes. The inventors have observed mucin complexation and condensation in-vitro using a turbidometric assay. It has been found by the inventors that these mucin-condensing materials improve glucose tolerance in animal models. Without limiting the invention to a specific mechanism of action, the inventors propose that insoluble mucin/polymer complexes formed in the upper GI tract comprise an occlusive barrier layer capable of preventing contact between dietary contents and the luminal wall of the duodenum. This occlusive luminal barrier interferes with neurogastric signaling thereby providing a significant improvement in glucose tolerance. The inventors have found that therapeutically useful barriers can be formed in-situ by mucin-condensing materials as described above. In addition, the inventors have found that therapeutically effective luminal barriers are also formed by mucin-thickening materials which reduce the permeability of the duodenal mucin layer, and by mucoadhesive materials capable of forming a barrier layer in the duodenum.

Another factor that enables targeting of the preferred mucin-interacting agents of this invention to the duodenum is the nature of the mucus found in the duodenum. The mucin-interacting compositions of this invention have a higher propensity to interact, complex and bind with the loosely adhered mucin layer. The ratio of the loose to firm mucus layer is much higher in duodenum compared to the stomach. The abundance of loosely-bound mucus in the duodenum enhances the diffusion of the mucin-interacting agents into the loose layer and enables preferential creation of the barrier in the duodenum.

Without limiting the invention to a specific mechanism of action, the inventors recognize that effective compounds of the mucin-condensing class are generally cationic and therefore also capable of binding to bile acids in the GI tract. It is foreseen in this invention that compounds capable of mucin-complexation are uniquely able to act therapeutically through two distinct mechanisms: an occlusive barrier-formation mechanism (described in detail above), and a bile acid binding mechanism.

The modulation of glucose homeostasis through the action of bile acid binders or sequestrants has recently attracted great interest. Published studies have demonstrated increased release of glucagon-like peptide-1 (GLP-1) from the intestine following administration of a bile acid binding agent. In certain instances, translocation of the bile acids from the early GI tract to the distal gut (e.g., colon and/or rectum) is thought to stimulate L-cells and/or certain receptors (TGRS) thereby providing a therapeutic effect for treating obesity and/or diabetes. This therapy is considered especially effective because L-cell concentrations rise significantly in the distal gut. Hence, bile acids are thought to have a much more potent secretory effect for metabolic hormones. Published data suggests that higher concentrations of bile salts in the distal small bowel and/or colon enhances the secretion of enteroendocrine peptides (e.g., GLP-1, GLP2, oxyntomodulin, PYY) from L-cells that are present in the distal GI tract.

Compounds which have been developed for bile acid sequestration for use in the present invention include various ion exchange polymers. One such polymer is cholestyramine, a copolymer of divinylbenzene and trimethylammoniummethyl styrene. More recently, various polymers have been developed which are characterized by hydrophobic substituents and quaternary ammonium radicals substituted upon an amine polymer backbone (described in U.S. Pat. Nos. 5,428,112, 5,430,110, 5,462,730 and 6,083,497 the disclosures of which are incorporated herein by reference in their entireties). Other commercially available bile acid sequestrant drugs for use in the present invention include colesevelam (commercially known as Welchol®), cholestyramine (commercially known as Questran®, Cholybar®), colestipol (commercially known as Colestid®), and sevelamer (commercially known as Renagel® and Renvala®).

Embodiments of the invention include one or more mucin interacting components defined above optionally with agents for the modification of viscosity, color, taste, and shelf-stability. Embodiments my combine mucin-thickening and mucin-complexing agents together in a single formulation.

In one embodiment, chitosan (Ch) is formulated along with hydroxyethylcellulose (HEC) and dextran (Dex). In embodiments, the Ch is used in the range of 0.1-10.0% (w/w), HEC is used in the range of 0.1-2.0% (w/w), and Dex is used in the range of 0.05-1.0% (w/w). In one embodiment, the Ch/HEC/Dex ratio is 3/0.5/0.3.

In another embodiment, chitosan (Ch) is formulated along with hydroxyethylcellulose (HEC). In embodiments, Ch is used in the range of 0.1-10.0% (w/w) and HEC is in the range of 0.1-2.0% (w/w). In one embodiment, the Ch/HEC ratio is 3/1.5.

In another embodiment, chitosan (Ch) is formulated along with Laponite XLG®. In embodiments, Ch is used in the range of 0.1-10.0% (w/w), and laponite is used in the range 0.1-3.0% (w/w). In one embodiment, the Ch/Laponite ratio is 3/1.

Colloidal bismuth subcitrate is very effective in the treatment of gastro-duodenal disorders and is known to act via several mechanisms. It has antimicrobial properties, and can inhibit enzyme activity. It causes an increase in mucus glycoprotein secretion and can also bind to the mucus layer to act as a diffusion barrier. Other bismuth carboxylate salts such as bismuth subsalicylate, are also known to have these gastroprotective and cytoprotective properties.

In an embodiment, bismuth carboxylate compounds are administered orally along with mucoadhesive components. In one embodiment, bismuth subsalicylate is compounded with hydroxylethyl cellulose and poly(vinylpyrolidone) in a ratio of 7%/0.5%/3% (w/w).

In yet another embodiment, bismuth carboxylate compounds are administered orally along with mucin-complexing and mucoadhesive components. In one embodiment, bismuth subsalicylate is compounded with chitosan (Ch) and hydroxylethyl cellulose (HEC) in a ratio of 7%/3%/3% (w/w).

In other embodiments, tannic acid is combined with hydroxyethylcellulose (HEC). In various embodiments, tannic acid is used in the range of 0.1-10.0% (w/w) and HEC is used in the range of 0.1-2.0% (w/w). In one embodiment, the tannic acid/HEC ratio is 2%/0.5% (w/w).

In other embodiments, tannic acid is combined with chitosan. Tannic acid is used in the range of 0.1-10.0% (w/w) and chitosan is used in the range of 0.1-10.0% (w/w). In one embodiment, the tannic acid/chitosan ratio is 1/1.

In any of the embodiments disclosed herein, chitosan (Ch) having a molecular weight greater than about 25, 50, 90, 130, 150, 190, 220, 310 or 400 kDa may be used. Further any such chitosan may have a degree of deacetylation of greater than about 60, 65, 70, 75, 80, 85, 90 or 95%. In embodiments, a composition of the invention includes chitosan, optionally in combination with water or an aqueous buffer at a concentration of greater than or equal to about 0.1, 0.5, 1, 2, 3, 4, 5, 6, 7, 8, 9 or 10% by weight.

As discussed herein, the physical barrier is delivered to the gastrointestinal tract of the subject via a formulation selected from the group consisting of an ingestible syrup, a liquid, a gel, an ointment, a powder, and a tablet.

In such embodiments, the one or more impermeable or semipermeable barrier forming materials can be delivered to the gastrointestinal tract of the subject via an endoscope, a nasal or oral feeding tube, and combinations thereof. In further embodiments, the one or more impermeable or semipermeable barrier forming materials are sprayed onto the inner intestinal lumen of the subject. In particular embodiments, the spraying is done endoscopically. In the liquid embodiments, the coating on the lining of the small intestines may be non-contiguous.

In embodiments, the physical barrier or a formulation thereof is passed by natural digestive processes of the subject. In yet other embodiments, the physical barrier is removable or reversible by the ingestion of a liquid or solvent.

In some embodiments, no component of the physical barrier is absorbed from the gastrointestinal tract during the formation of the physical barrier or retention period thereafter. In particular embodiments, each of the components of the physical barrier are delivered in non-toxic doses.

In some embodiments, the presently disclosed subject matter provides a method for treating T2DM and/or obesity in a subject in need of treatment thereof, the method comprising disrupting one or more signaling pathways in the GI tract, e.g., in the proximal small intestine or duodenum, by partially excluding a region thereof from contact with luminal contents. As used herein, the term "neurohormonal signaling pathways" means communication from one region of the body to another via either nerves or secreted substances such as hormones. In some embodiments, the partial exclusion is achieved by lining a region of the duodenum with one or more impermeable or semipermeable barrier forming components as disclosed herein. In particular embodiments, the partial exclusion is stochastically distributed within the duodenum or proximal small intestine. Importantly, the presently disclosed methods disrupt one or more signaling pathways in the GI tract by partially excluding a region thereof from contact with luminal contents without significantly interfering with nutrient absorption. In some embodiments, the metabolic disorder is selected from the group consisting of obesity, pre-diabetes, insulin resistance, type 1 diabetes mellitus, type 2 diabetes mellitus, glucose impairment, hypertension, dyslipidemia, and hyperlipidemia.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In particular embodiments of the presently disclosed methods, the subject is a mammalian subject.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The following examples are provided to further illustrate the embodiments of the present invention, but are not intended to limit the scope of the invention. While they are typical of those that might be used, other procedures, methodologies, or techniques known to those skilled in the art may alternatively be used.

Example 1

Formulations

This example sets forth illustrative formulations of the invention.

TABLE 1

Formulation 1

| Ingredient | Amount |
|---|---|
| Chitosan | 1.0 g |
| Acetic Acid | 1.0 g |
| DI Water | qs (to 100 g) |

TABLE 2

Formulation 2

| Ingredient | Amount |
|---|---|
| Chitosan | 0.30 g |
| Acetic Acid buffer (pH = 4.7) | qs (to 100 g) |

TABLE 3

Formulation 3

| Ingredient | Amount |
|---|---|
| Chitosan | 3.0 g |
| hydroxyethylcellulose | 0.50 g |
| dextran | 0.30 g |
| sodium dihydrogenphosphate dihydrate | 0.25 g |
| 1N sodium hydroxide | q.s. |
| hydrochloric acid | q.s. |
| sterile purified water | q.s. to 100 g total weight |

Formulation 3 was prepared as follows. A viscous, aqueous solution was prepared by mixing chitosan and water using Brinkmann Heidolph Electronic High-Torque Overhead Stirrer and a 4-blade 40 mm propeller rotating at 200-300 rpm. An aqueous solution of hydrochloric acid was added with stirring to give a clear gel. An aqueous solution of, sodium dihydrogenphosphate dihydrate and was added with stirring to give a clear solution. Hydroxyethylcellulose and dextran were added with stirring to give a clear solution. The pH was adjusted to 5.0-6.0 with an aqueous solution of sodium hydroxide. The resulting product was mixed further for 30 minutes.

TABLE 4

Formulation 4 - Chitosan/HEC

| Ingredient | Amount - Weight Percent |
|---|---|
| Chitosan | 3.0 g |
| Glycyrrhetinic acid | 0.06 |
| Maltodextrin | 6.00 |
| Propylene glycol | 2.94 |
| Potassium sorbate | 0.4 |
| Sodium benzoate | 0.4 |
| Hydroxyethyl cellulose | 1.5 |
| Hydrogenated castor oil PEG-40 | 0.27 |
| Disodium EDTA | 0.1 |
| Benzalkonium chloride | 0.5 |
| Perfume (Glycyrrhiza Comp. 2717) | 0.16 |
| Sodium saccharin | 0.1 |
| Purified Water | q.s. to 100 g weight |

Formulation 4 was prepared as follows. Water was placed in a 500 ml beaker fitted with a Brinkmann Heidolph Electronic High-Torque Overhead Stirrers overhead mixer and a 4-blade 40 mm propeller. While stirring at 500 rpm, a mixture of potassium sorbate, sodium benzoate and disodium EDTA was added, followed by chitosan and maltodextrin. The mixture was stirred after each addition until complete dispersion of the components. Sodium saccharin and hydroxyethylcellulose were subsequently added, the mixture was subjected to vacuum and left under stirring at 800 rpm for 2-hours. Afterwards, hydrogenated castor oil 40/OE and perfume, benzalkonium chloride, and a mixture of propylene glycol and glycyrrhetinic acid were added in that order, stirring after each addition until complete dissolution of the components. When all additions were completed, the mixture was allowed to stir for an additional 30 minutes.

TABLE 5

| Formulation 5 - Chitosan/Laponite | |
|---|---|
| Ingredient | Amount - Weight Percent |
| Purified Water | q.s. to 100 g weight |
| Laponite XLG ® | 1.0 |
| 10% hydrochloric acid | c.a. 4.6 |
| benzyl alcohol | 1.50 |
| polysorbate 60 | 0.05 |
| Chitosan | 3.0 |
| 0.5% phosphoric acid | Qs |
| citric acid | 0.05 |
| sodium saccharin | 0.40 |
| Glycerin | 5.00 |

Formulation 5 was prepared as follows. A viscous, aqueous solution was prepared by adding Laponite XLG® to water using Brinkmann Heidolph Electronic High-Torque Overhead Stirrer and a 4-blade 40 mm propeller rotating at 800-1000 rpm for 1-hour. An aqueous solution of potassium hydroxide, citric acid, sodium saccharin, phosphoric acid and glycerin was added with stirring to give a clear solution. A solution of benzyl alcohol and polysorbate 60 was added with stirring to give a clear solution. Chitosan was added with an aqueous solution of hydrochloric acid with stirring to give a clear gel. The pH was adjusted to 5.0-6.0 with an aqueous solution of phosphoric acid. PVP was added and the resulting product was mixed further for 30 minutes.

TABLE 6

| Formulation 6 - Tannic acid | |
|---|---|
| Ingredient | Amount - Weight Percent |
| Purified Water | q.s. to 100 g total weight |
| Tannic acid | 2.0 g |

TABLE 7

| Formulation 7 - Tannic acid/CMC | |
|---|---|
| Ingredient | Amount - Weight Percent |
| Purified Water | q.s. to 100 g total weight |
| Tannic acid | 2.0 g |
| Carboxymethylcellulose (CMC) | 0.5 g |

TABLE 8

| Formulation 8 - Tannic acid/Chitosan | |
|---|---|
| Ingredient | Amount - Weight Percent |
| Purified Water | q.s. to 100 g total weight |
| Tannic acid | 2.0 g |
| Chitosan | 1.0 g |

Example 2

Mucoadhesive Viscosity Assay Using Rheometer

The rheological properties and flow behavior of all formulations are measured using a programmable Brookfield Model DV-IIIT rheometer (Brookfield Engineering Laboratories, Inc., USA). The rheometer is used with the SC4-18/13R spindle and small sample adaptor at 37.0±0.1 C. Stock solutions of chitosan are prepared (2.0% w/w) in DI water, 1% acetic acid, or 0.1M acetate buffer (pH=4.7). Dried mucin is hydrated with each medium by gentle stirring for 3 h at room temperature to yield a dispersion of 10% w/w. A 5 gram aliquot of mucin dispersion is mixed on a vortex mixer with a 5 gram aliquot of the polymer solution in the corresponding media to give a concentration of 1.0% w/w with respect to polymer. The final concentration of mucin is 5% w/w. All materials are kept at 37.0±0.1 C for 1 h to equilibrate prior to analysis. Samples of each formulation are added to the chamber of the rheometer and allowed to equilibrate for at least 2 min prior to testing. Viscosity measurements are made in triplicate within a 0-50 sec^-1 shear rate range. In each case the viscometric experiments are performed only once on each solution sample.

For the mucin/polymer combinations, the expected viscosity ($\eta$ exp), the viscosity enhancement ($\eta$ enhance), and the relative viscosity enhancement ($\eta$ rel) are defined in equations (1)-(3).

$$\eta exp = \eta poly + \eta muc \quad (1)$$

$$\eta enhance = \eta obs - \eta exp \quad (2)$$

$$\eta rel = \eta obs / \eta exp \quad (3)$$

The $\eta$ poly and $\eta$ muc are the viscosity of the polymer and mucin solutions alone, respectively. In cases where the observed viscosity ($\eta$ obs) is found to be greater than the expected viscosity ($\eta$ exp), then the polymer is designated as a mucin-thickening agent.

The viscosity enhancement ($\eta$ enhance) is equivalent to the viscosity component of bioadhesion and is related to the force of mucoadhesion (F) at shear rate ($\sigma$) as in equation 4.

$$F = (\eta enhance)(\sigma) \quad (4)$$

Active mucin thickeners are ranked according to their relative low shear force of mucoadheison. The preferred mucin-thickening agents of this invention are observed to provide significant viscosity enhancements and force of mucoadhesion.

Example 3

Mucin Complexation Turbidity Assay

Terms—These terms are used throughout the Examples.
MW=Molecular weight
LCS=50-190 kDa Chitosan
MCS=190-310 kDa Chitosan
PAA=poly(acrylic) acid
HEC=hydroxyethylcellulose
CA=Carbopol 974P-NF
HA=Hyaluronic Acid
PVP=Polyvinylpyrrolidone
PVP-DMA=Polyvinylpyrrolidone-co-2-dimethylaminoethyl methacrylate
PVP-CVA=Polyvinylpyrrolidone co-vinyl acetate
GC=Commercial Gelclair™
RC=Commercial Rincinol™
MG=Commercial MuGard™
PVA=Mowiol (Polyvinyl Alcohol mw 205K)
PMVE-MA=Poly(methyl vinyl ether-alt-maleic acid)
PDC=Poly(diallyldimethylammonium chloride)
Methods
Mucin Preparation
Porcine gastric mucin at 1% (w/v) was suspended in 100 mM acetate buffer solution (ABS), pH 4.7 overnight for complete dispersion. The dispersion was then centrifuged at 1,400 rpm at 4 degrees Celsius centrifuge machine. Supernatant was collected and refrigerated until use.

All polymers were dissolved in 100 mM ABS, ph 4.7 using a standard weight/volume (polymer/solvent) ratio and mixed using a magnetic stirrer at 400 RPM. Polymers were pipetted with mucin using a 1:1 ratio in clear 96 well plates. Plates were incubated in 37 degrees Celsius for 60 minutes. After the incubation period, each well was read using a standard spectrophotometer at a wavelength of 500 nm. Kinetic measurements were run using the same machine with at a frequency of 10 seconds for 20 minutes.

Results

Figure 6:
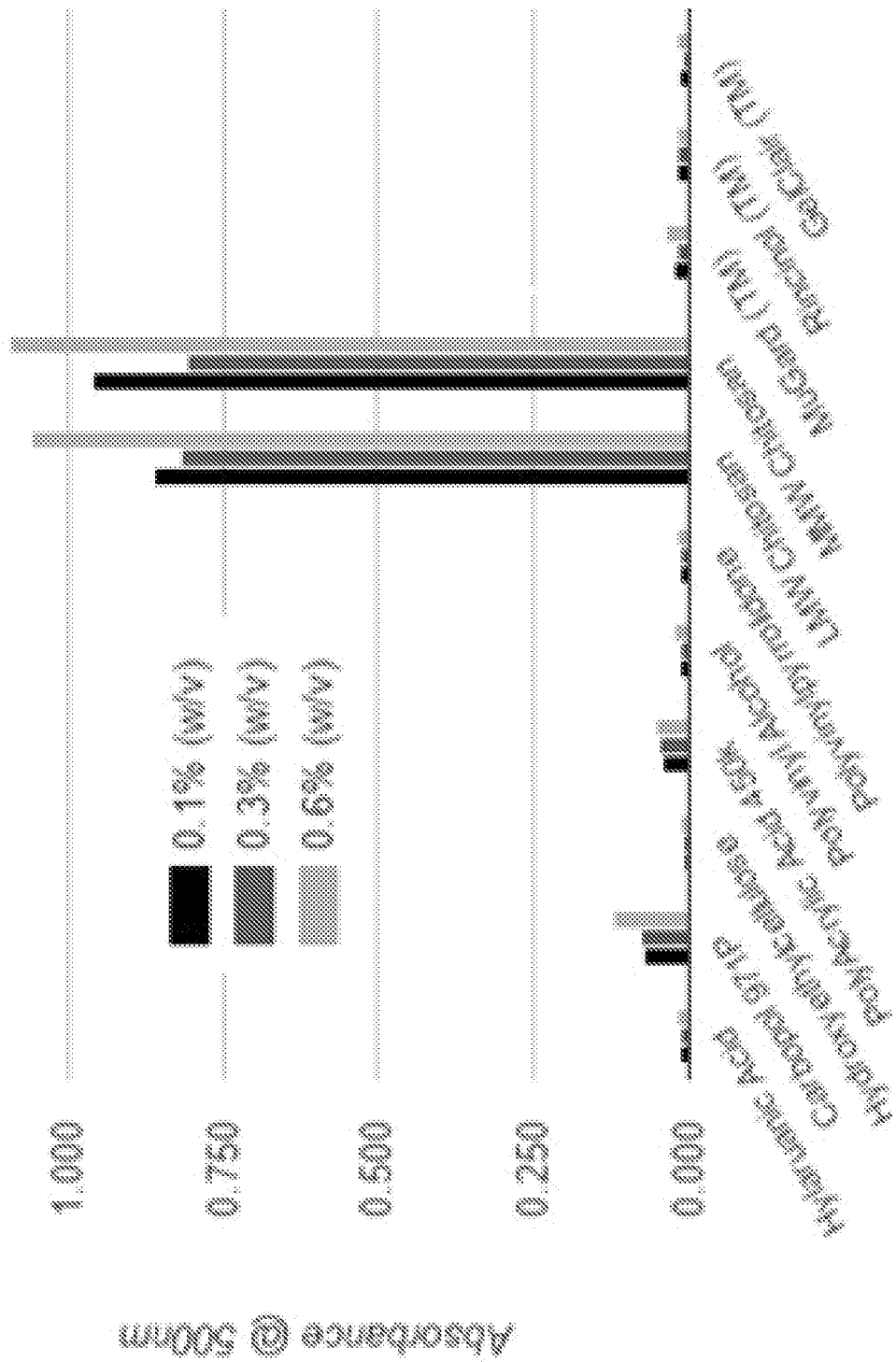
FIG. 6 is a graphical display representing data relating to embodiments of the disclosure.

Cationic polymers like chitosan resulted in the most turbidity when compared to other polymers (FIG. 6).

Figure 7:
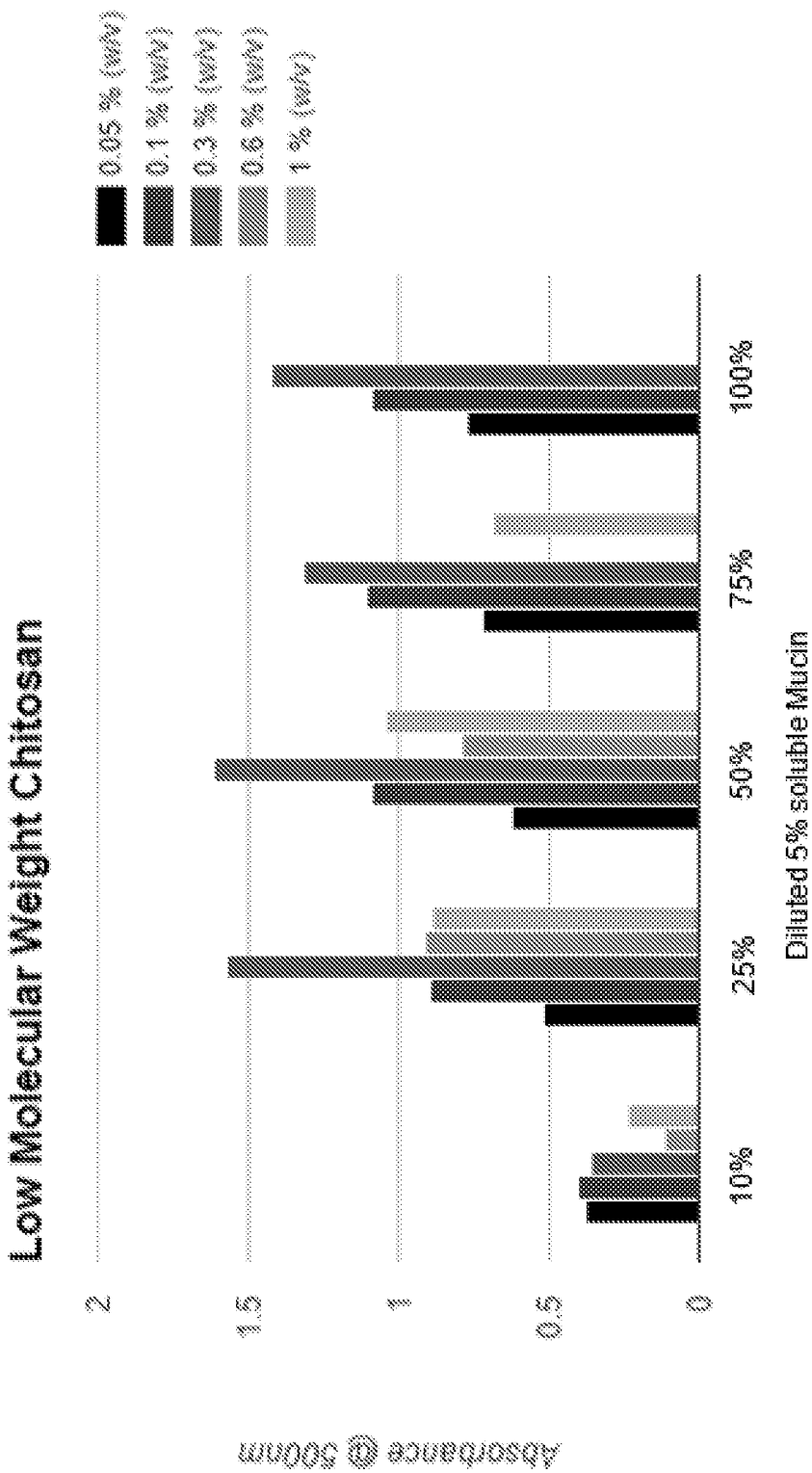
FIG. 7 is a graphical display representing data relating to embodiments of the disclosure.
Figure 8:
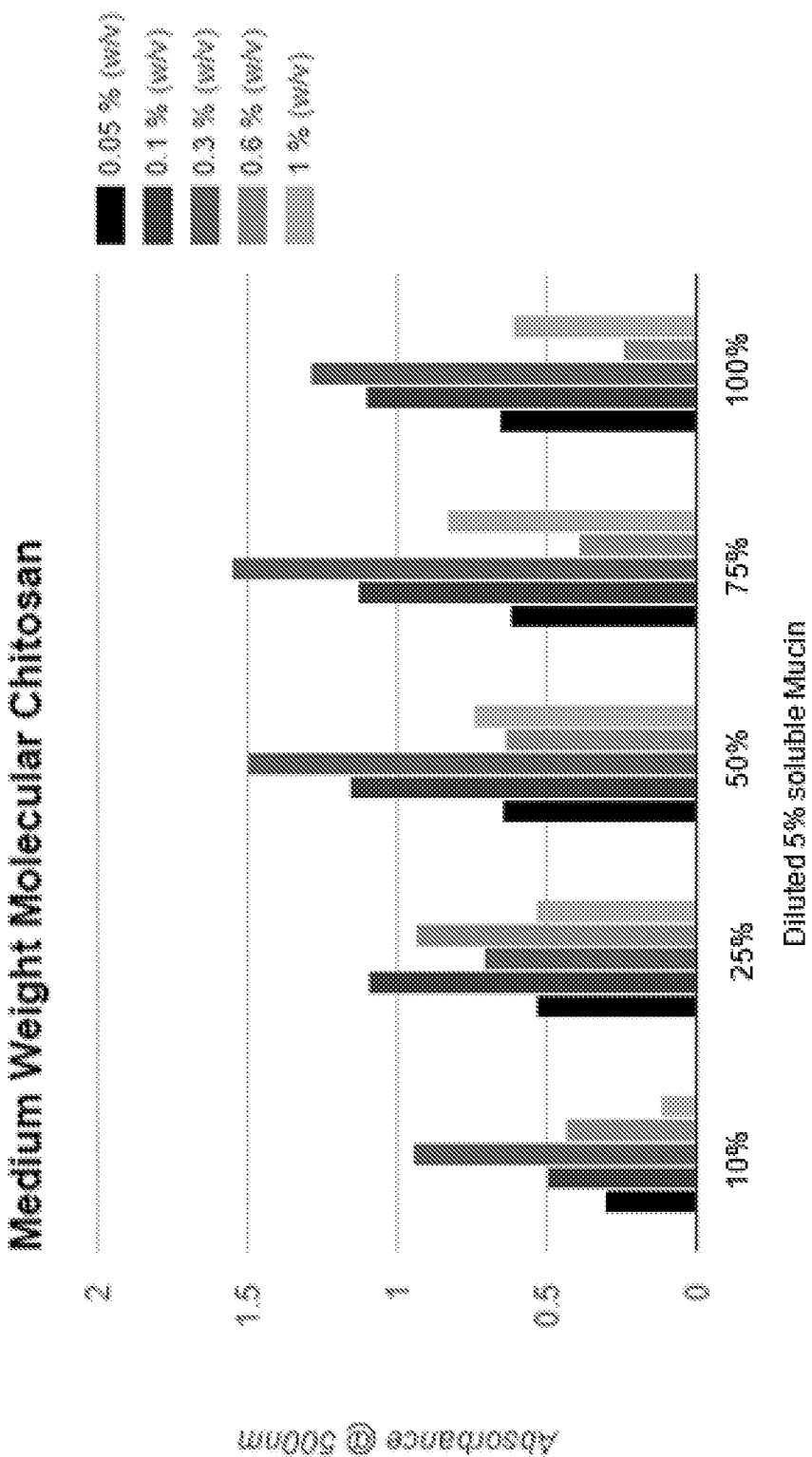
FIG. 8 is a graphical display representing data relating to embodiments of the disclosure.

Turbidity assay performance is sensitive to the concentration of both chitosan and mucin. FIGS. 7 and 8 show results from an experiment in which various chitosan concentrations were examined. Effective mucin complexion was observed in this experiment for 0.3% chitosan solutions.

Figure 9:
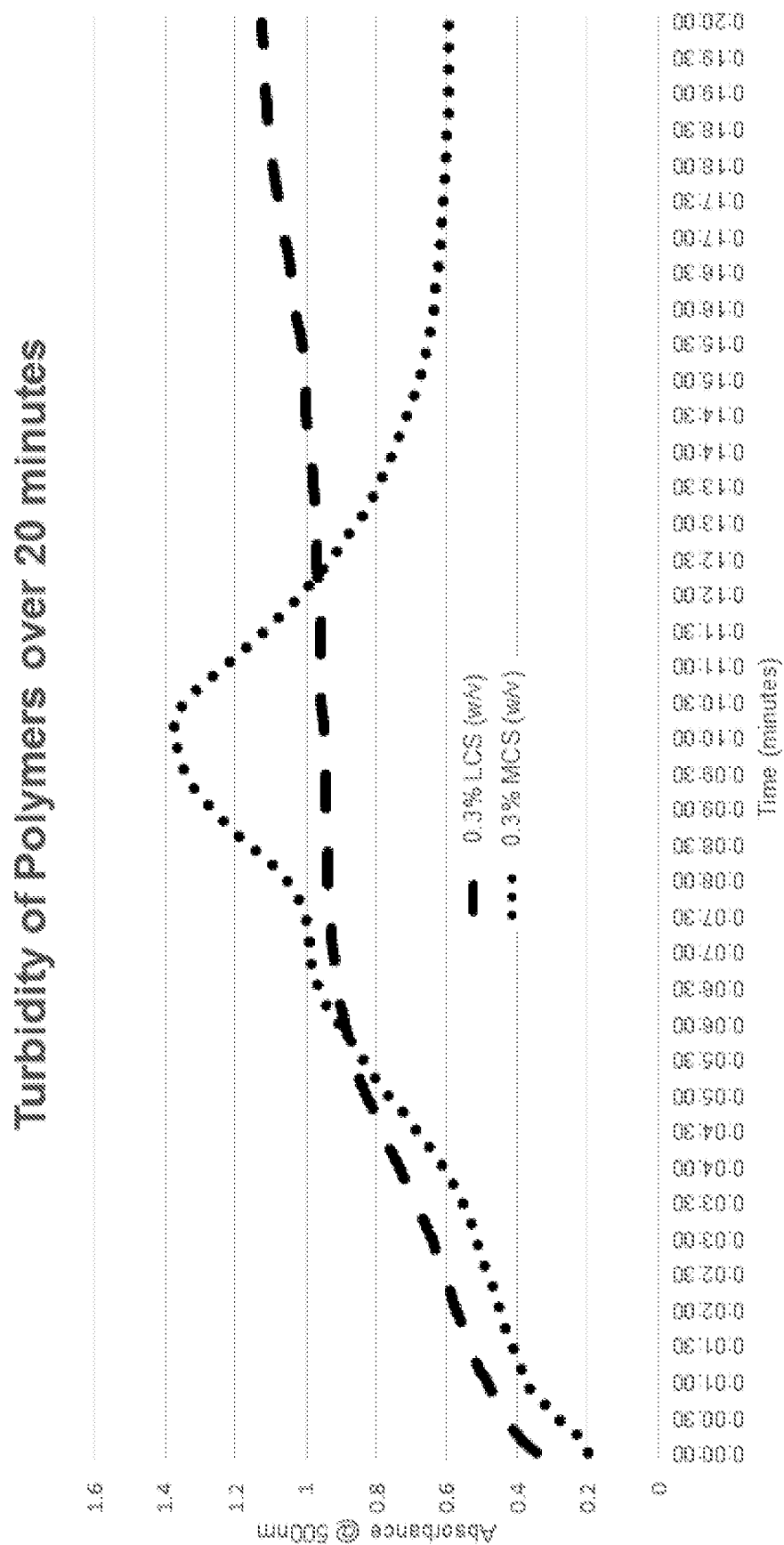
FIG. 9 is a graphical display representing data relating to embodiments of the disclosure.

Further investigation into the 0.3% LCS and 0.3% MCS shows rapid complexation of chitosan with mucin (FIG. 9). Rapid in-situ formation of a polymer lining has clinical significance. Diabetic patients are used to taking medication before meals. The basis of our approach requires the disruption of neurohormonal pathways in the GI tract as food is passing through the duodenum. This data suggests that the described embodiment would allow patients to swallow a mucosal lining that would become active and impermeable within 10-60 minutes of ingestion.

Figure 19:
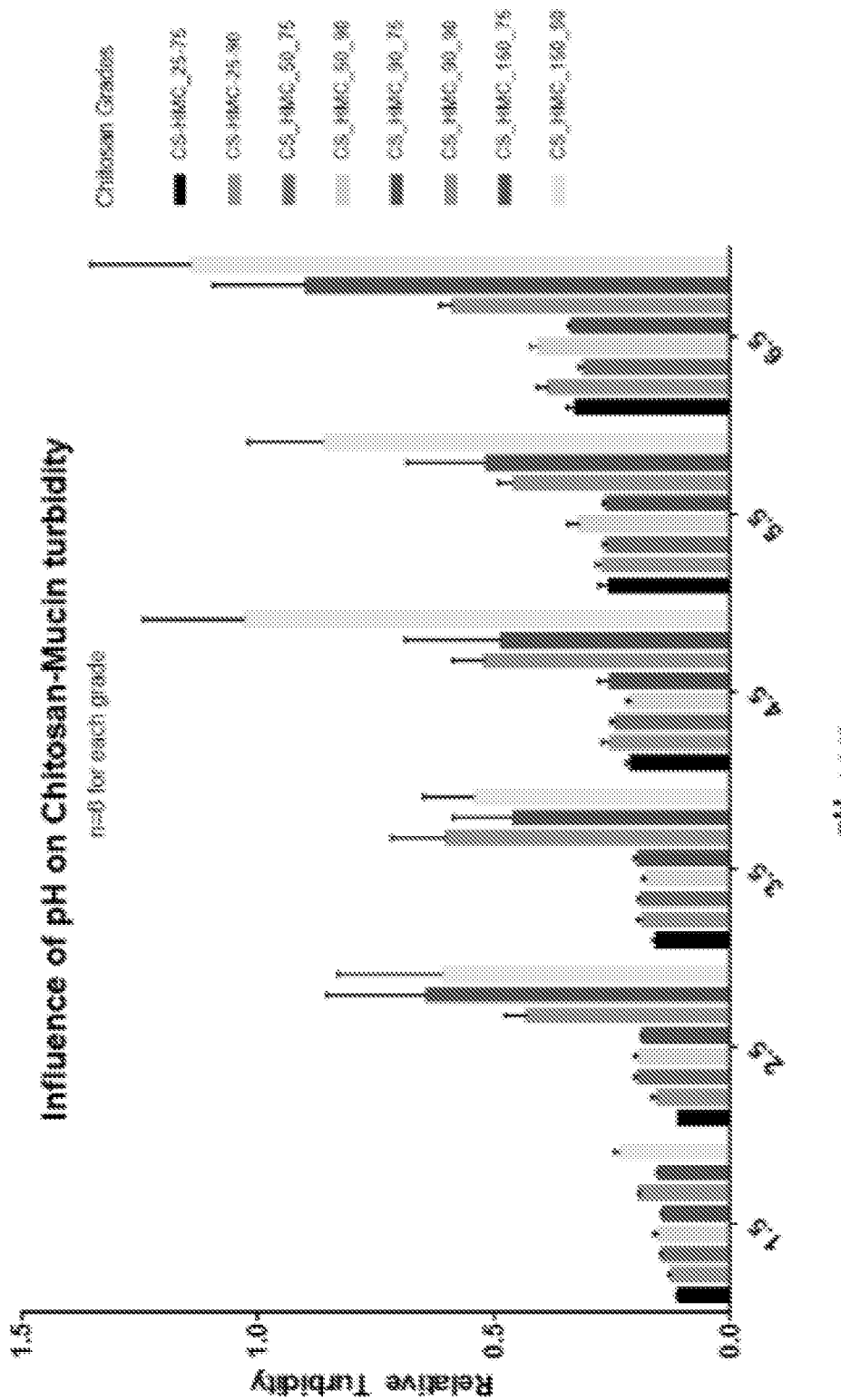
FIG. 19 is a graphical display representing data relating to embodiments of the disclosure.

Further investigation of various molecular weight chitosans showed that an increase in molecular weight and, to a more limited degree, an increase in percent deacetylation intensified targeted complexation of chitosan with mucin in different pH environments which is beneficial for duodenal specific delivery (FIG. 19). Notations for FIG. 19 samples are as follows: CS=chitosan, HMC=Supplier code, $3^{rd}\#$=Molecular Weight, $4^{th}\#$=Deacetylation %. For example, CS_HCM_25_75 is a formulation including chitosan (25 kDa) having 75% deacetylation. Concentration of chitosan for each sample was 1% by weight.

Example 4

Occlusive Barrier Permeability Assay

Methods

A simulated mucosal environment was created in order to evaluate the barrier properties of mucoadhesives using a transwell plate system. Specifically, 0.75 μL of a 1% w/v porcine stomach mucin (Sigma-Aldrich, USA) solution was deposited onto each cellulose nitrate membrane insert (pore size: 0.45 μm, Merck Millipore, Germany). Immediately following, 0.75 μL of the mucoadhesive polymer or Acetate Buffer Solution (ABS) was deposited on top of the mucin layer. The mucin and polymer were oscillated at 37 degree C. at 120 rpm for 30 minutes to enable interaction between the mucin and polymer. Then 600 of ABS was deposited outside the insert and 200 μL of glucose at 0.8 mg/dL concentration was added to the top of the transwell system. The samples were collected and plated from the receiving chambers at 60 minutes. The samples were analyzed with GAGO-20™ Glucose kit (Sigma Aldrich, USA) was used to measure the diffusion of glucose through the membrane. The permeability inhibition of the mucoadhesive polymers was calculated as follows.

$$\text{Inhibition}(\%) = \left(\frac{(A control - A treatment)}{A control}\right) \times 100$$

Results

Figure 10:
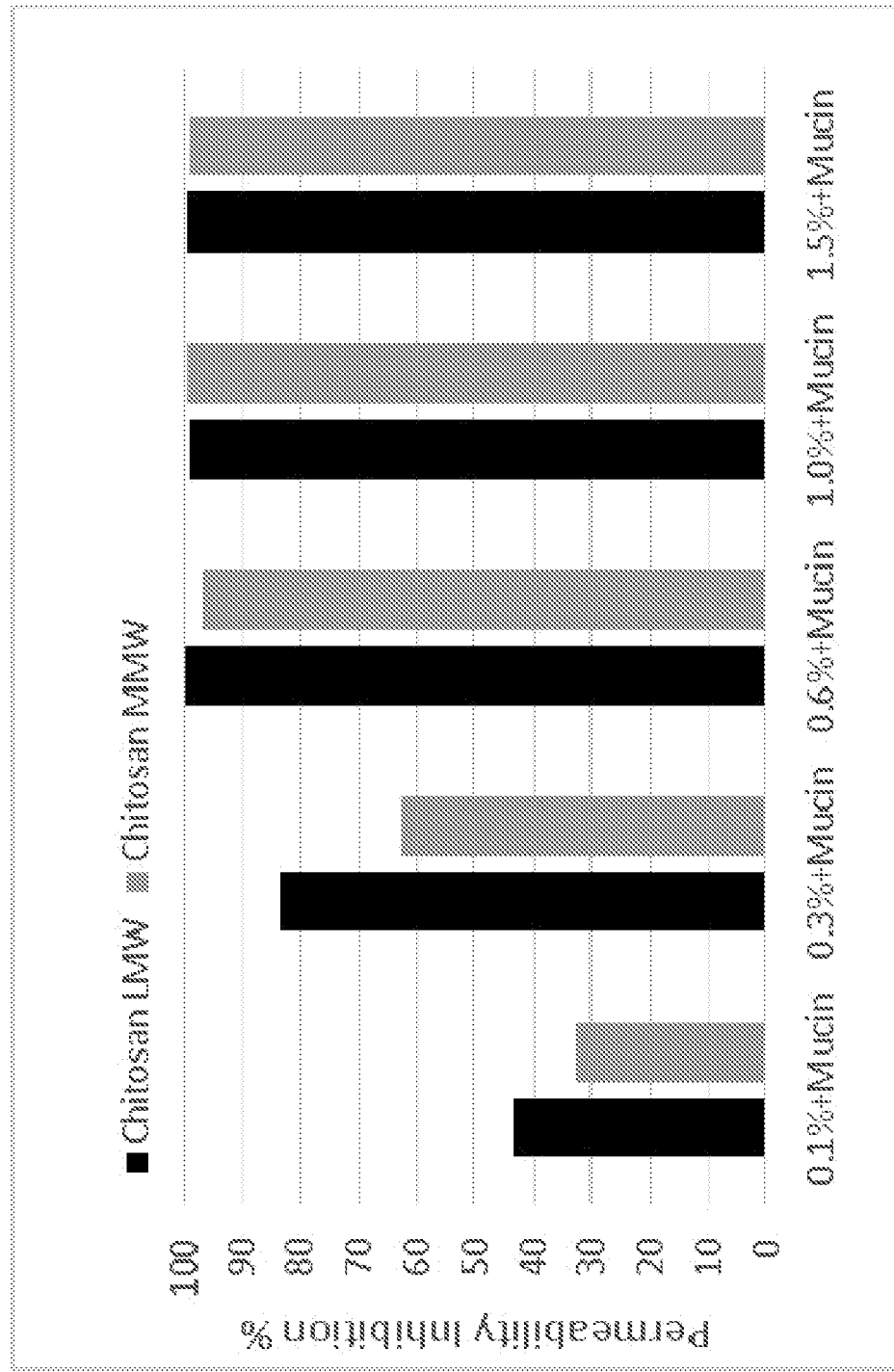
FIG. 10 is a graphical display representing data relating to embodiments of the disclosure.

The chitosan/mucin interaction was further studied by comparing a range of molecular weights for inhibition percentage. Enhanced permeability inhibition is demonstrated in-vitro by increasing molecular weights for chitosans while keeping concentrations consistent (FIG. 10).

Figure 18:
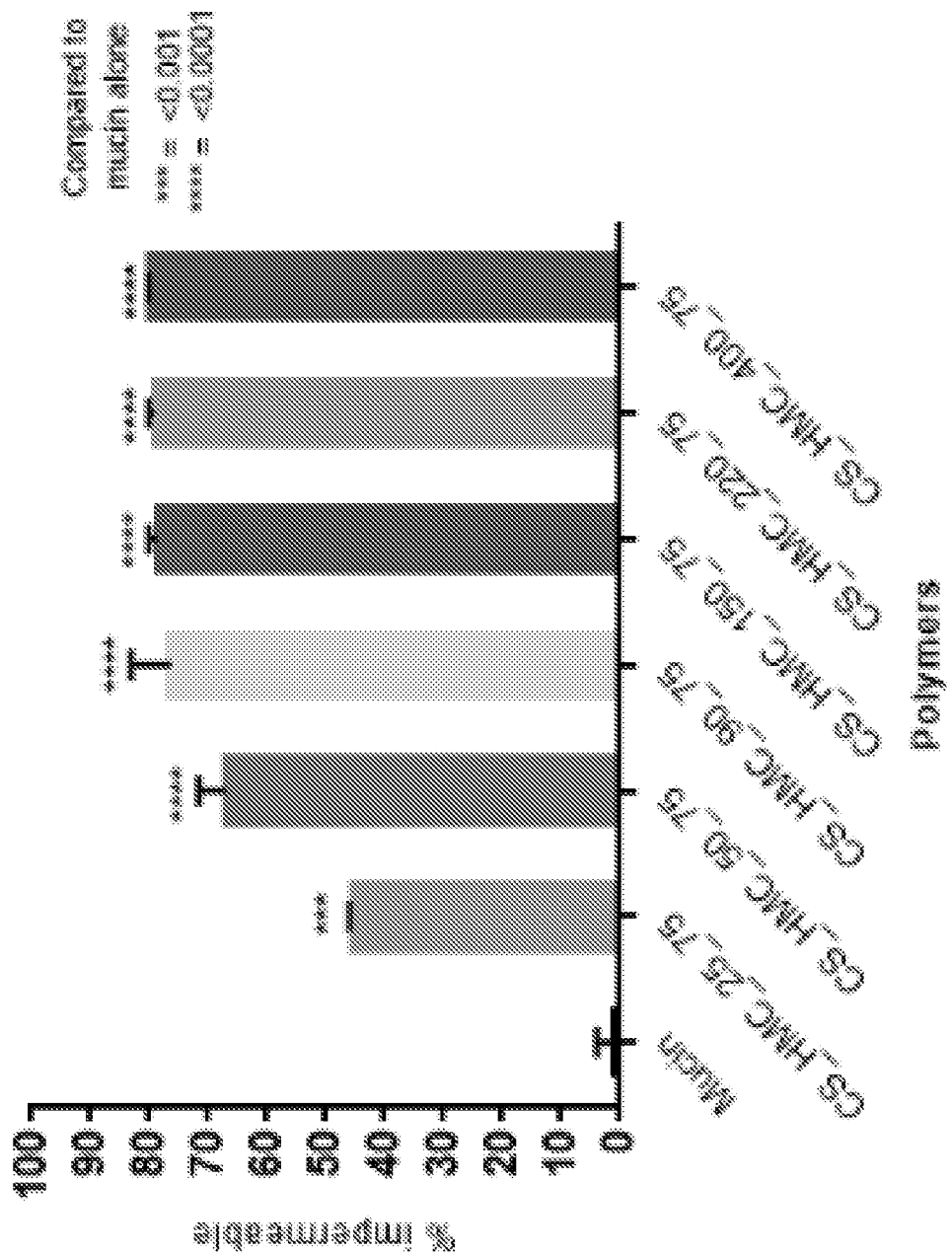
FIG. 18 is a graphical display representing data relating to embodiments of the disclosure.

The chitosan/mucin interaction was further studied by comparing various molecular weight chitosans (25-400 kDa) having 75% deacetylation; concentration remained constant. A general trend of increased impermeability was observed with increasing molecular weight (FIG. 18). Notations for FIG. 18 samples are as follows: CS=chitosan, HMC=Supplier code, $3^{rd}\#$=Molecular Weight, $4^{th}\#$=Deacetylation %. For example, CS_HCM_25_75 is a formulation including chitosan (25 kDa) having 75% deacetylation. Concentration of chitosan for each sample was 1% by weight.

Example 5

Rat Oral Glucose Tolerance Test

Methods

Testing was conducted to investigate the efficacy of a mucoadhesive lining in the treatment of T2DM. In some versions of this experiment, infusion catheters were surgically implanted in Sprague Dawley adult male rats (250 g-300 g). In some versions of this experiment, infusion catheters were surgically implanted in Zucker Diabetic Fatty (ZDF) or Goto-Kakizaki (GK) adult male diabetic rats (250 g-400 g). The catheters ran from the intestinal lumen one centimeter distal to the pylorus and exited out of the animal's upper back. After implantation of the infusion catheter, animals were allowed to recover for at least one week and housed individually at 19° C.-22° C. and 40%-60% humidity with a 12-hour light-dark cycle. In other versions of the present example, rodents were not surgically implanted with infusion catheters. Instead, infusions were made by oral gavage.

Prior to experiment, all rats were fasted for 18 hours and allowed water. Animals were split into a control group, which received 0.9% saline and a treatment group, which received a mucoadhesive compound of interest, unless otherwise specified below. Unless otherwise specified, a single infusion was administered through the duodenal cannula in a 1 mL dose at the specified concentration. 45 minutes after the final gavage of saline or mucoadhesive, baseline blood glucose levels were taken. Oral gavage of 0.1 g/mL glucose solution (40% concentration, 1g/kg rat) was given immediately following the baseline blood glucose reading. Glucose tolerance test samples were taken from each rat at specified time points over a 2-3 hour time period following the glucose administration.

Results

Figure 11:
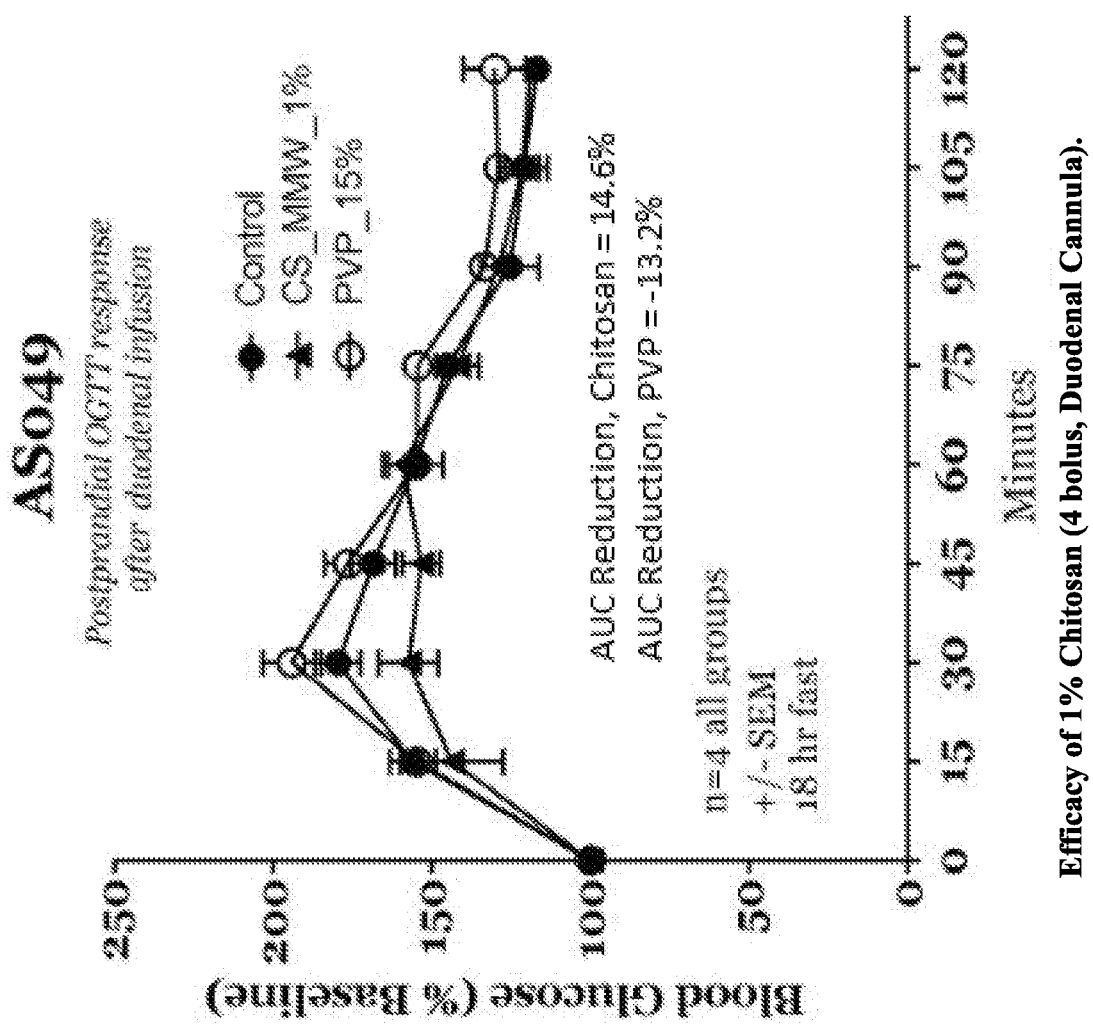
FIG. 11 is a graphical display representing data relating to embodiments of the disclosure.

Study ID: AS049 (FIG. 11)

Mucoadhesive formulation: 1% (w/w) MMW chitosan (190-310 kDa Chitosan) dissolved in 1% acetic acid (Formulation 1; CS_MMW_1%)

Control: 0.9% NaCl

Dosing: 4 infusions of 0.85 mL through duodenal cannula/catheter. Infusions were separated by 30 minute intervals.

Discussion: As seen in the figure above, 1% chitosan in 1% acetic acid (Formulation 1) is effective at blunting the glucose curve in a 2 hour oral glucose tolerance test administered to healthy, Sprague-Dawley rodents. When considering translation to humans with T2DM, the blunting of this peak is significant. It is well known that uncontrolled spikes in blood sugar are responsible for many of the macro- and micro-vascular complications associated with T2DM. In order to determine the dosing effect Formulation 1, another experiment was performed with identical parameters but only 2 boluses of 0.85 mL, effectively halving the total dose of mucoadhesive polymer.

Figure 12:
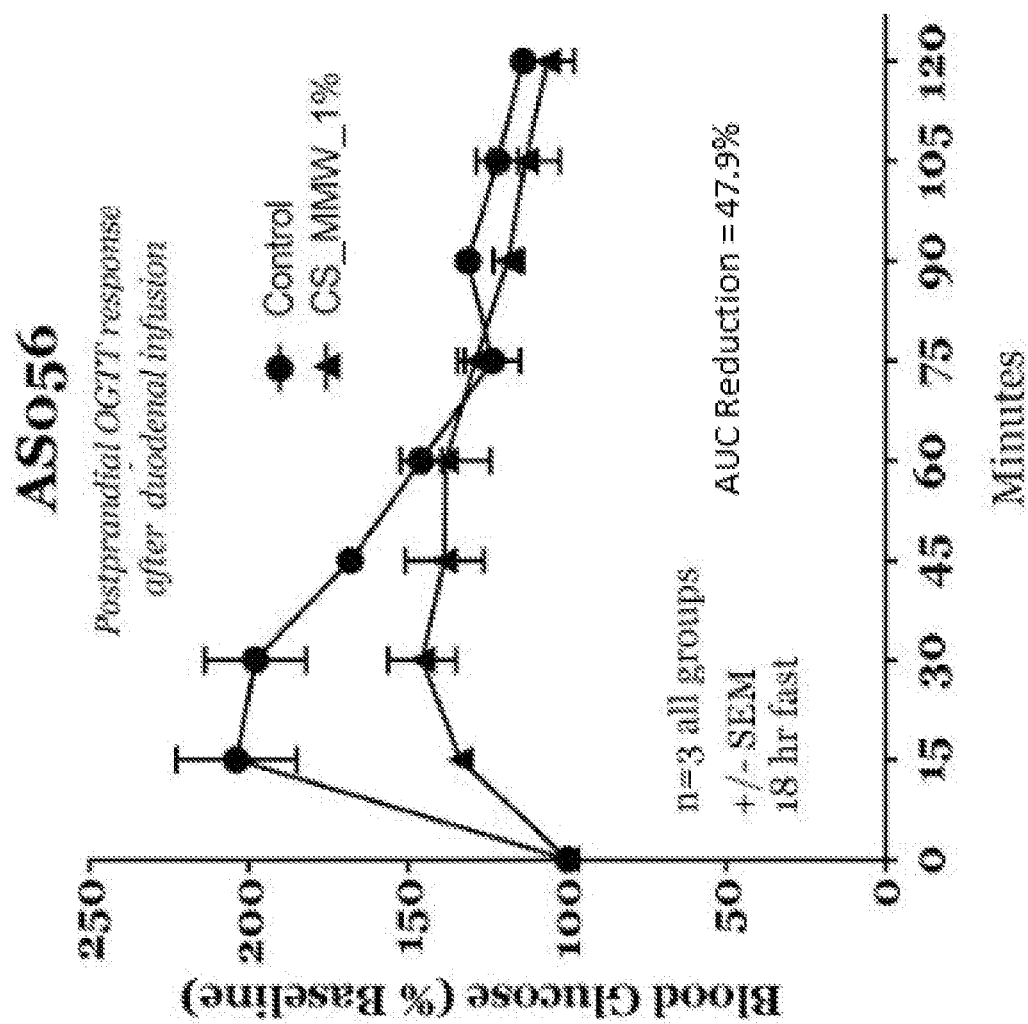
FIG. 12 is a graphical display representing data relating to embodiments of the disclosure.

Study ID: AS056 (FIG. 12)
Mucoadhesive formulation: 1% (w/w) MMW chitosan (190-310 kDa Chitosan) dissolved in 1% acetic acid (Formulation 1; CS_MMW_1%)
Control: 0.9% NaCl
Dosing: 2 infusions of 0.85 mL through duodenal cannula/catheter. Infusions were separated by 30 minute intervals.
Interpretation: Again, 1% chitosan in 1% acetic acid (Formulation 1) is effective at blunting the glucose curve in a 2 hour oral glucose tolerance test administered to healthy, Sprague-Dawley rodents. However, in this experiment, only 2 boluses of 0.85 mL were administered. Instead of seeing a diminished effect on the glucose curve, a similar efficacious result is achieved. This supports the hypothesis that inhibiting nutrient absorption is not the primary mechanism of the intestinal barrier. Instead, coating a specific region of the proximal gut leads to a therapeutic effect. Doubling that dose does not necessarily lead to a greater therapeutic effect, as would be expected if inhibiting nutrient absorption were the primary mechanism of action.

The 4 bolus and 2 bolus studies represent doses of 100 mg/kg and 50 mg/kg of MMW chitosan, respectively. The results of these experiments suggest that a clinically relevant dose of MMW chitosan is in the range of 10, 20, 30, 40, 50, 60, 70, 80, 90, 100, 110, 120, 130, 140, 150 mg/kg.

Study ID: AS046 (FIG. 11)
Mucoadhesive formulation: 15% polyvinylpyrilodone (PVP) in DI $H_2O$
Control: 0.9% NaCl
Dosing: 4 infusions of 0.85 mL through duodenal cannula. Infusions were separated by 30 minute intervals.
Interpretation: Results suggest that 15% PVP, alone does not exhibit the same therapeutic effect as PVP when combined with other constituents, such as hyaluronic acid (HA). Given the viscosity of 15% PVP, this important result shows that delayed/slowed gastric emptying is not responsible for the therapeutic effect seen in the 2 hour oral glucose tolerance test.

Study ID: AS062 (data not shown)
Mucoadhesive formulation: 0.3% Chitosan in 1% acetic acid (Formulation 1)
Control: 0.9% NaCl
Dosing: 4 infusions of 0.85 mL through duodenal cannula. Infusions were separated by 30 minute intervals.
Interpretation: Prophetically, similar or better efficacy as 1% chitosan in acetic acid is expected as predicted by the turbidity assay.

Study ID: AS063 (data not shown)
Mucoadhesive formulation: 7.3% PVA in 1% acetic acid and DI $H_2O$
Control: 0.9% NaCl
Dosing: 4 infusions of 0.85 mL through duodenal cannula. Infusions were separated by 30 minute intervals.

Interpretation: Prophetically, it is expected that PVA is a negative control, highlighting the importance of mucoadhesion and high performance on assays like the turbidity assay.

Figure 13:
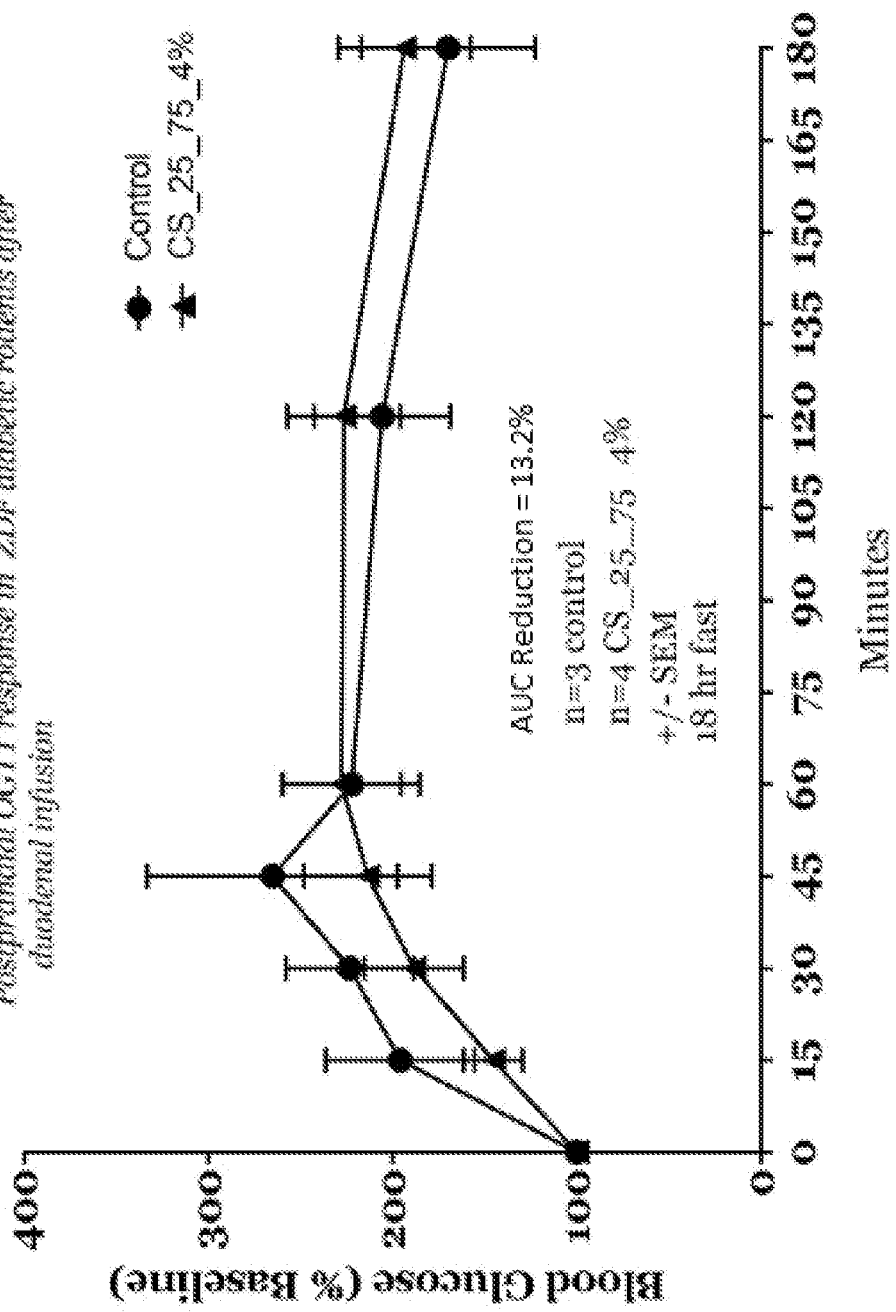
FIG. 13 is a graphical display representing data relating to embodiments of the disclosure.

Results
Study ID: ZDF018 (FIG. 13)
Compound: Chitosan
Formulation: 4% Chitosan (25 kDa, 75% deacetylation) (w/w) in 1% acetic acid buffer.
Subclass: Mucin-interacting Agent
Delivery: Duodenal Cannula
Strain: Zucker Diabetic Fatty Rodent
Peak comparison (Treat. vs. Cont.): 228% vs. 265%
Reduction in incremental AUC: CS_25_75_4%=13.2% (see FIG. 13).

Figure 14:
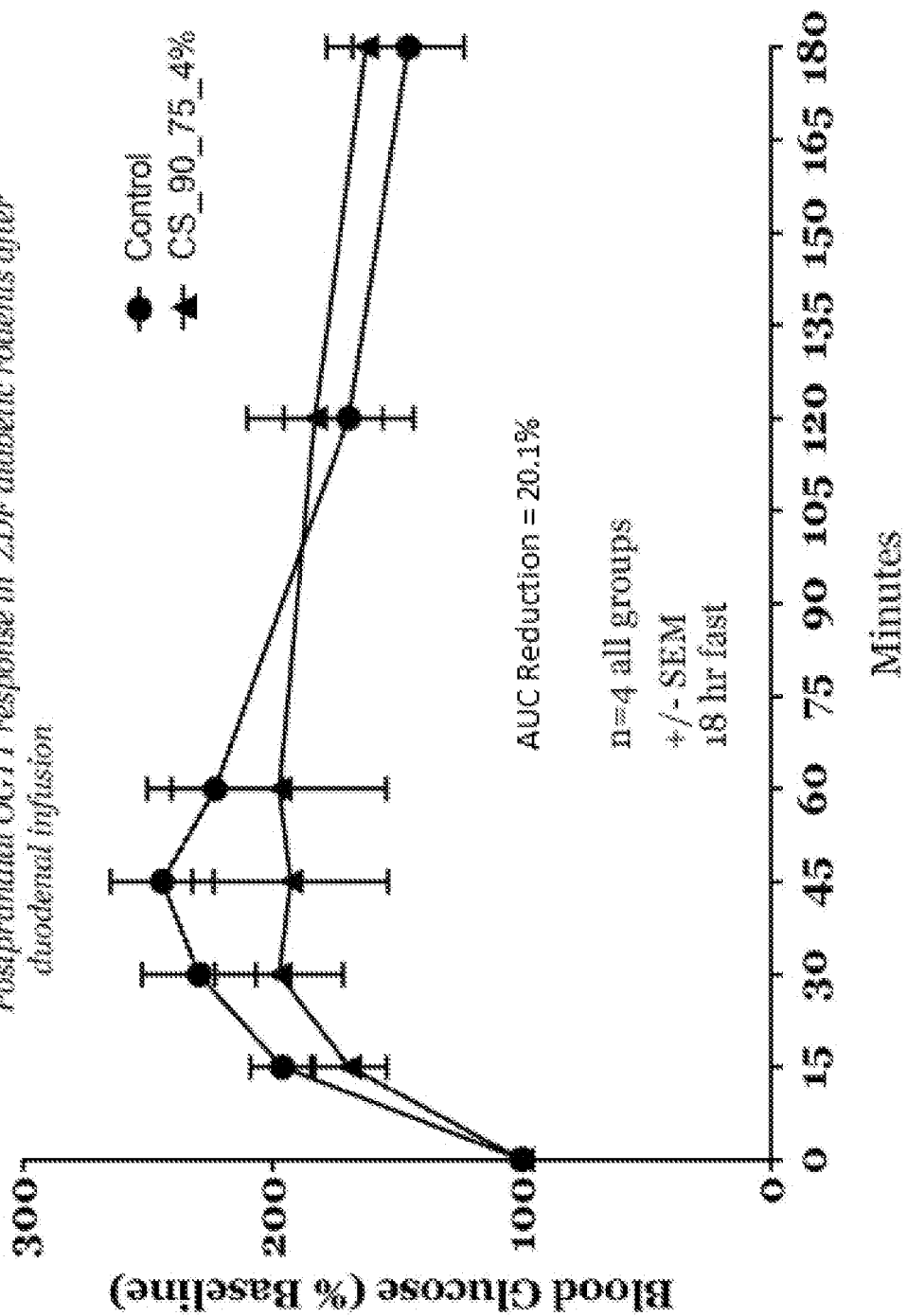
FIG. 14 is a graphical display representing data relating to embodiments of the disclosure.

Study ID: ZDF019 (FIG. 14)
Compound: Chitosan
Formulation: 4% Chitosan (90 kDa, 75% deacetylation) (w/w) in 1% acetic acid buffer.
Subclass: Mucin-interacting Agent
Delivery: Duodenal Cannula
Strain: Zucker Diabetic Fatty Rodent
Peak comparison (Treat. vs. Cont.): 197% vs. 244%
Reduction in incremental AUC: CS_90_75_4%=20.1% (see FIG. 14).

Figure 15:
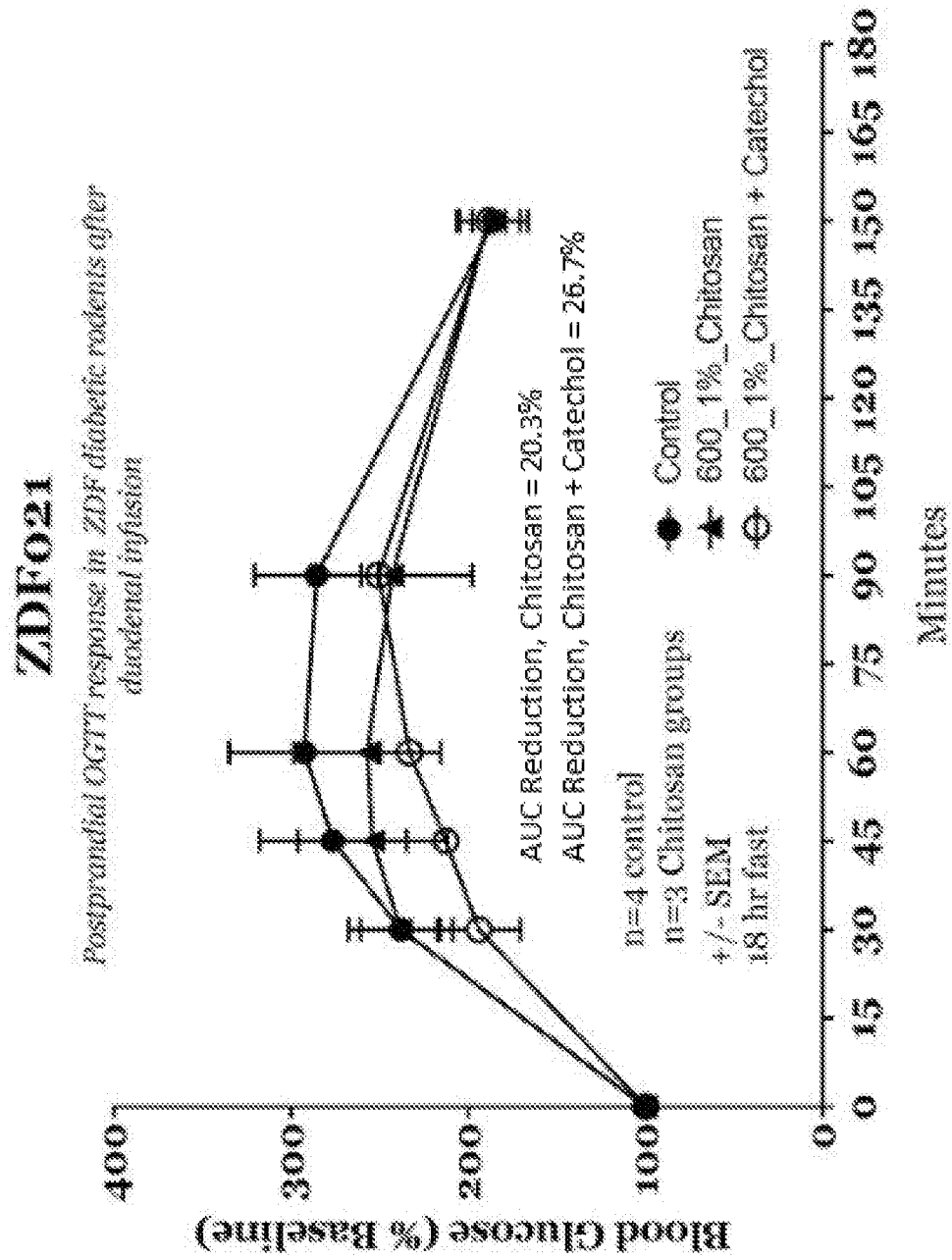
FIG. 15 is a graphical display representing data relating to embodiments of the disclosure.

Study ID: ZDF021 (FIG. 15)
Compound: Chitosan and Chitosan-catechol derivative
Formulation: 1% Chitosan (600 kDa) (w/w) in 1% acetic acid buffer.
Subclass: Mucin-interacting Agent
Delivery: Duodenal Cannula
Strain: Zucker Diabetic Fatty Rodent
Peak comparison (Chiotsan. vs. Chitosan-Catechol vs. Cont.): 257% vs. 251% vs. 293%
Reduction in incremental AUC: CS 600_75_1%=20.3%; CS+Cat_600_75_1%=26.7% (see FIG. 15).

Figure 16:
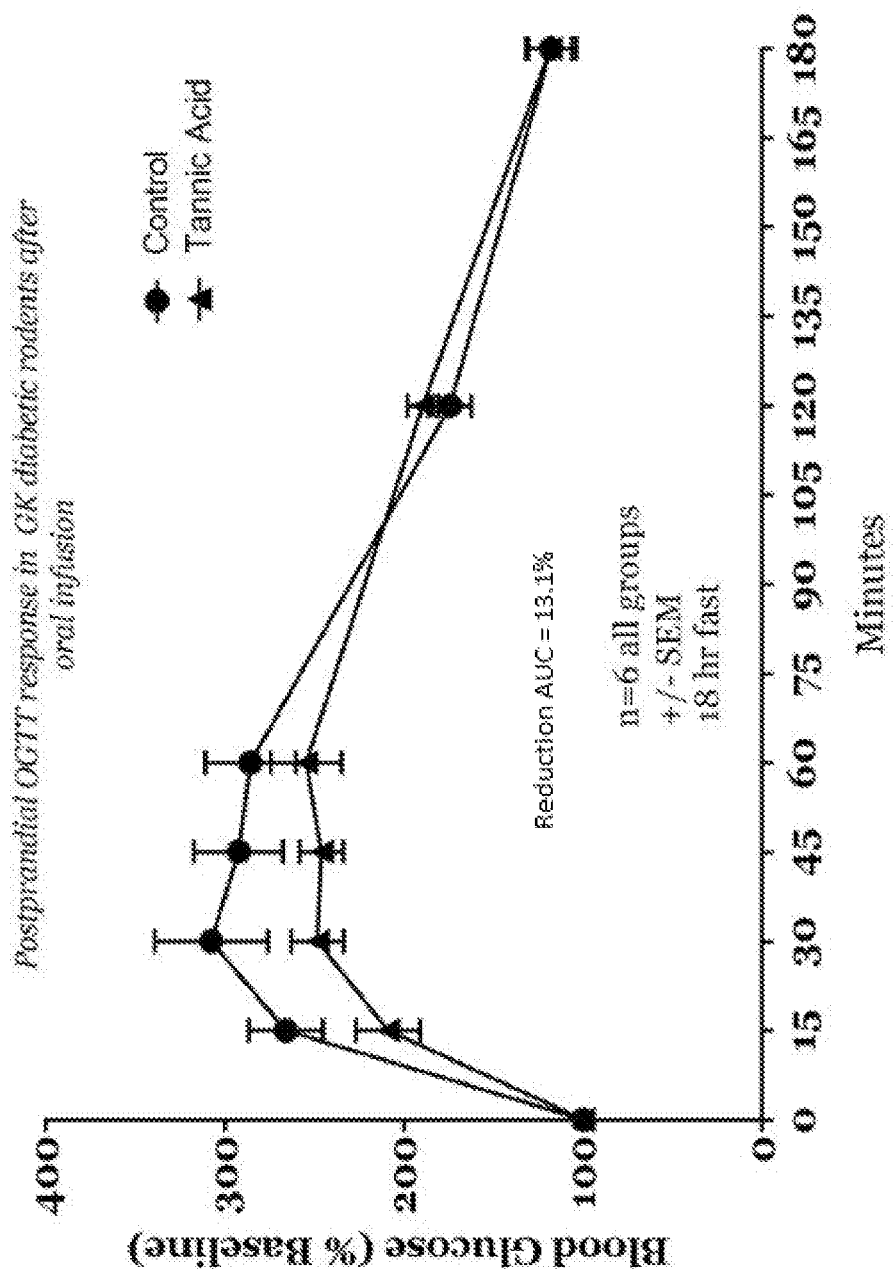
FIG. 16 is a graphical display representing data relating to embodiments of the disclosure.

Study ID: GK001-002 (FIG. 16)
Compound: Tannic Acid
Formulation: 4% tannic acid (w/w) in water.
Delivery: Oral Gavage
Subclass: Mucin Interacting Agent
Strain: Goto-Kakizaki Rodent
Peak comparison (Treat. vs. Cont.): 257% vs. 300%
Reduction in incremental AUC: TA_4%=13.1%

Figure 17:
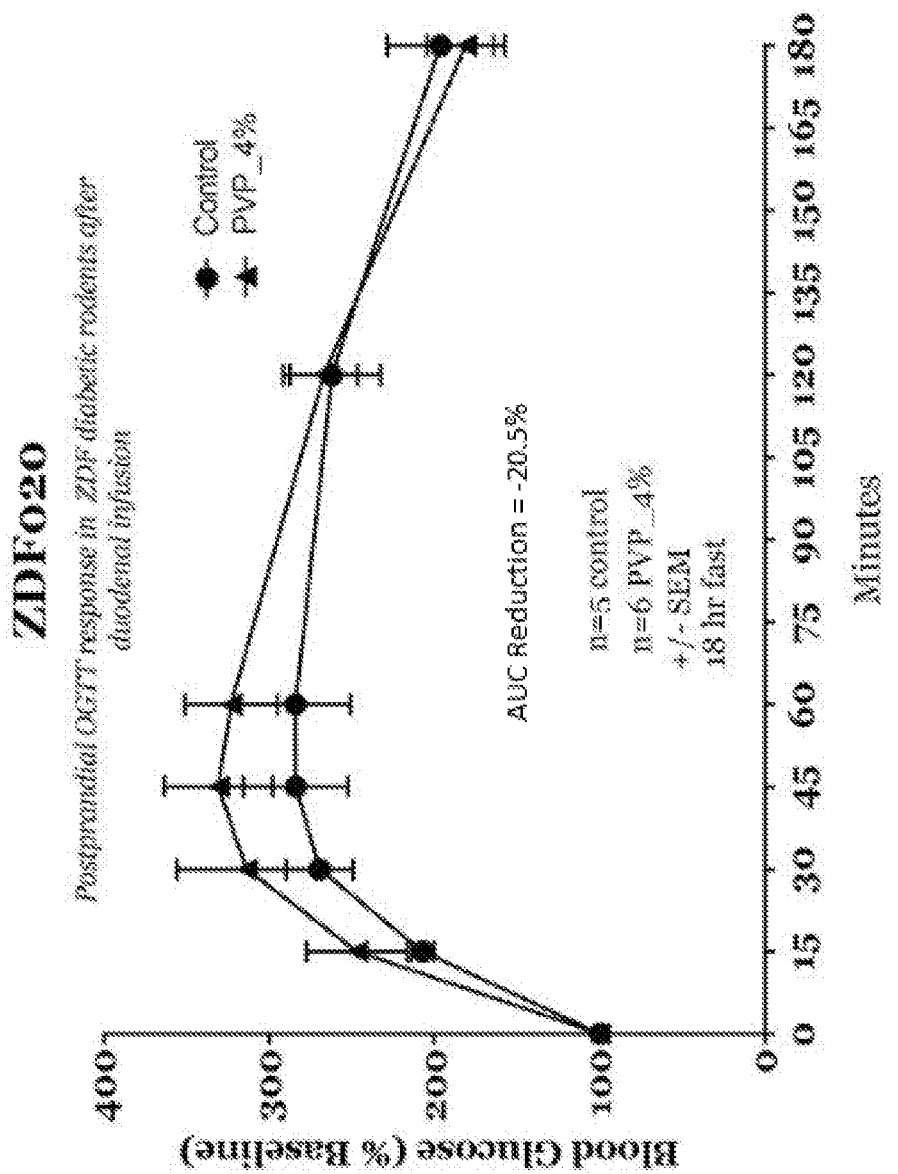
FIG. 17 is a graphical display representing data relating to embodiments of the disclosure.

Study ID: ZDF020 (FIG. 17); a negative example using non-mucoadhesive interacting agents, e.g., PVP.
Compound: Polyvinylpyrrolidone (PVP)
Formulation: 4% Concentration of 150 kDa PVP
Subclass: General Mucoadhesive
Peak comparison (Treat. vs Cont.): 316% vs. 279%
Reduction in incremental AUC=−20.5% (see FIG. 17).

Example 6

Region Specific Effect of Mucoadhesive in the Rodent Oral Glucose Tolerance Test Methods
Testing is conducted to investigate the region specific effect of a mucoadhesive lining in the treatment of T2DM. Infusion catheters are surgically implanted into two groups of Sprague Dawley adult male rats (250 g-300 g) with access ports exiting out of the animal's upper back. In the first group (referred to as duodenal group), the catheters enter the intestinal lumen one centimeter distal to the pylorus. In the second group (referred to as the jejunal group), the catheters enter the intestinal from the Ligament of Treitz. After implantation of the infusion catheter, animals are allowed to recover for at least one week and housed individually at 19° C.-22° C. and 40%-60% humidity with a 12-hour light-dark cycle. Prior to experiment, all rats are fasted for 18 hours and allowed water. Animals in both the duodenal and jejunal groups are split into a control group (n=4), and gavaged with 0.9% saline and a treatment group (n=4), and gavaged with the mucoadhesive compound of interest. The infusions are administered through the cannulas in four equal doses separated by 30 minute intervals. Half an hour after the fourth gavage of saline or mucoadhesive, baseline blood glucose levels are taken. Oral gavage of 0.1 g/mL glucose solution (lg/kg rat) is given immediately following the baseline blood glucose reading. Glucose tolerance test samples were taken from each rat at 0, 15, 30, 45, 60, 75, 90, 105 and 120 minutes after the glucose administration.

Example 7

Mucoadhesive Distribution Using Fluorescence

Materials

Sprague Dawley rodents (250 g-300 g) were acquired from Harlan Laboratories with and without duodenal catheters implanted. 1% (w/v) chitosan in 1% acetic acid was tagged with fluorescein isothiocyanate (FITC) was prepared using a standard FITC protocol. Samples were read using black 96 well plates using a standard FITC protocol on a Beckman Coulter Spectrophotometer (Brea, Calif., USA).

Methods

Test groups received FITC chitosan orally or through the duodenum catheter. Control groups received 0.9% orally or through the duodenum. Rodents were sacrificed at t (mins) =0, t=30, t=60, t=90, t=120, and t=180. Starting with the stomach, samples in triplets were taken every 2 cm until 50 cm into the small intestines. Each sample was lightly rinsed in cold 0.9% saline before being homogenized and centrifuged at 10,000 RPM for 10 minutes at 4 degrees Celsius. The supernatant was plated in triplets using a 96 well plate.

Results

Figure 20A:
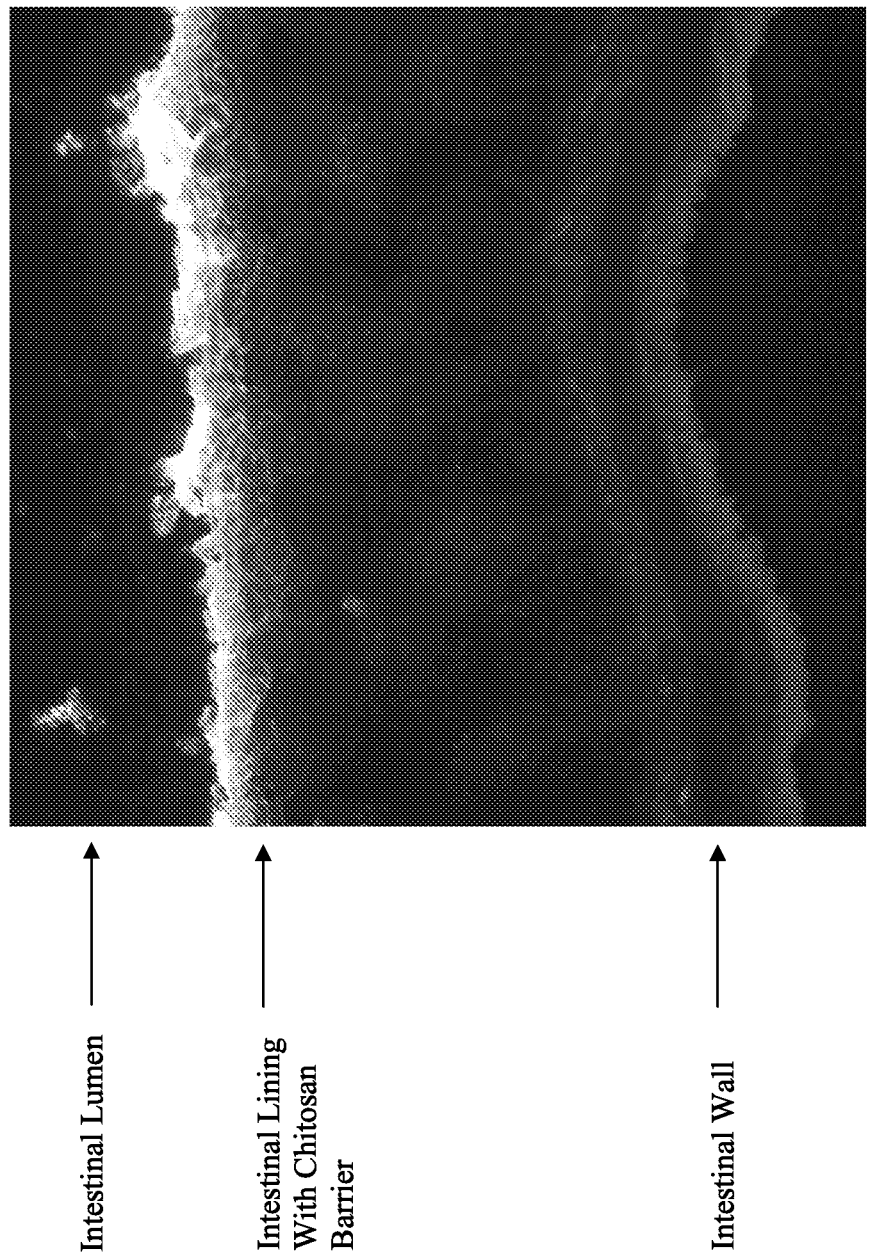
FIGS. 20A-20B are images of intestinal lining.
Figure 20B:
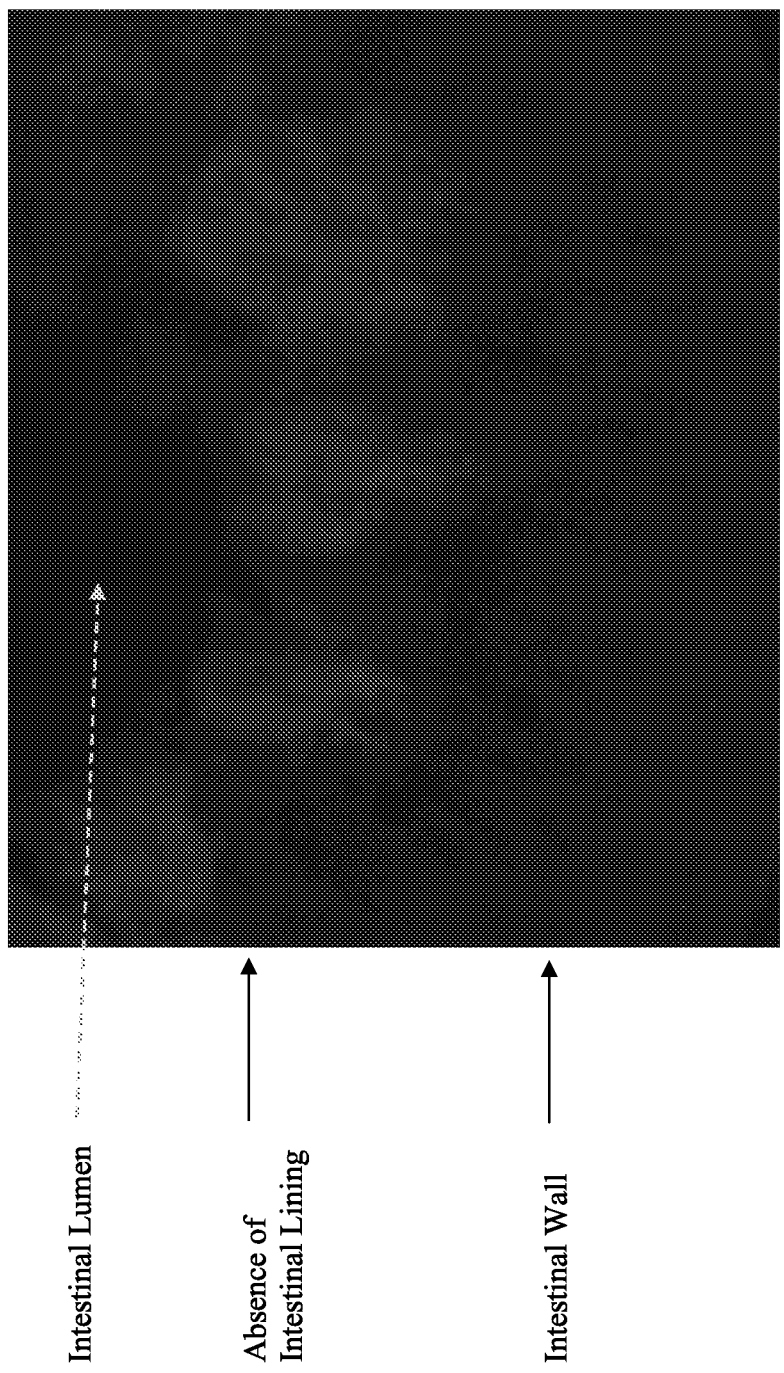

Fluorescent images of the lining were obtained to demonstrate retention of the polymer as an intestinal lining. See FIGS. 20A and 20B for representative images of the fluorescent intestinal lining.

Although the invention has been described with reference to the above examples, it will be understood that modifications and variations are encompassed within the spirit and scope of the invention.

What is claimed is:

1. A method for treating a metabolic disorder in a subject, comprising orally administering to a subject in need thereof a composition comprising a soluble, mucin-interacting polymeric amine as the sole active agent, wherein the composition is administered in an amount effective to form a physical barrier in situ in the gastrointestinal (GI) tract of the subject between the intestinal lining and the luminal contents by interaction of mucin resident in the duodenum and the polymeric amine.

2. The method of claim 1, the metabolic disorder is selected from the group consisting of obesity, pre-diabetes, insulin resistance, type 1 diabetes mellitus, type 2 diabetes mellitus, glucose impairment, hypertension, and dyslipidemia.

3. The method of claim 1, wherein the soluble mucin-interacting polymeric amine is a chitosan or a chitosan derivative.

4. The method of claim 3, wherein the chitosan derivative is selected from trimethyl chitosan, chitosan glycol, chitosan glycol trimethyl ammonium iodide and thiolated chitosan.

5. The method of claim 1, wherein the soluble mucin-interacting polymeric amine is a polyamine selected from polyethylenimine, hydroxyethyl polyethylenimine, poly(allylamine), poly(diallylamine), poly(diallyldimethylammonium chloride), polyamidoamine dendrimers and glycidol-substituted polyamines.

6. The method of claim 1, wherein the soluble mucin-interacting polymeric amine is an amine functionalized polymer selected from poly(vinylpyridine), poly(vinylimidazole), poly(vinylaniline), poly(vinylamine) and their derivatives or copolymers.

7. The method of claim 1, wherein the soluble mucin-interacting polymeric amine is an amine containing acrylamide and methacrylamide copolymers, acrylamidopropyltrimonium chloride copolymers or poly[2-(dimethylamino)ethyl] methacrylate copolymers.

8. The method of claim 1, wherein the physical barrier forms in the duodenum.

9. The method of claim 8, wherein the physical barrier begins at about the pyloric sphincter and extends for up to about 30 cm distal along the GI tract therefrom.

10. The method of claim 1, wherein the composition comprising the soluble mucin-interacting polymeric amine is in an aqueous solution.

11. The method of claim 2, wherein the metabolic disorder is type 2 diabetes mellitus.

12. The method of claim 1, where the physical barrier does not diminish nutrient absorption.

13. The method of claim 1, with the proviso that the soluble mucin-interacting polymeric amine is not a chitosan or a chitosan derivative.

* * * * *